US006413967B1

(12) United States Patent
Gray et al.

(10) Patent No.: US 6,413,967 B1
(45) Date of Patent: *Jul. 2, 2002

(54) INHIBITION OF NOVEL CALCIUM ENTRY PATHWAY IN ELECTRICALLY NON-EXCITABLE CELLS ACTING AS AN ANTI-PROLIFERATIVE THERAPY

(75) Inventors: Lloyd S. Gray; Doris M. Haverstick; John J. Densmore; Gabor Szabo, all of Charlottesville, VA (US)

(73) Assignee: The University of Virginia Patents Foundation, Charlottesville, VA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/413,229

(22) Filed: Mar. 30, 1995

(51) Int. Cl.[7] .................... A61K 31/502; A61K 31/50
(52) U.S. Cl. ............... 514/252.1; 514/252.12
(58) Field of Search .............. 514/224.8, 226.2, 514/255, 252.1, 252.12

(56) References Cited

U.S. PATENT DOCUMENTS 4,599,340 A * 7/1986 Silver et al. ................ 514/227
4,861,770 A * 8/1989 Weiershausen et al. ...... 514/211
4,950,680 A * 8/1990 Taylor et al. ................ 514/356
5,565,560 A * 10/1996 Goulet et al. ............... 540/456
6,156,312 A * 12/2000 Leskovar .................. 424/144.1

OTHER PUBLICATIONS

Chemical Abstracts, *Neuroscience Letters*, 177(1–2):155–8, Aug. 15, 1994.

Chemical Abstracts, *British Journal of Pharmacology*, 113(3):861–8, Nov. 1994.

* cited by examiner

*Primary Examiner*—Theodore J. Criares
(74) *Attorney, Agent, or Firm*—Scully, Scott, Murphy & Presser

(57) ABSTRACT

The present invention provides methods for screening for voltage gated (VG)-selective inhibitors, novel VG-selective inhibitors, compositions containing the same, methods for inhibiting calcium entry into electrically non-excitable cells with said VG-selective inhibitors, methods for preventing proliferation of electrically non-excitable cells with said VG-selective inhibitors as well as methods of treating autoimmune diseases, preventing graft rejections, preventing apoptosis and treating cancer with the same.

8 Claims, 9 Drawing Sheets

INHIBITION OF NOVEL CALCIUM ENTRY PATHWAY IN ELECTRICALLY NON-EXCITABLE CELLS ACTING AS AN ANTI-PROLIFERATIVE THERAPY

BACKGROUND OF THE INVENTION

1. Field of the Invention

The present invention provides methods for screening for voltage gated (VG)-selective inhibitors, novel VG-selective inhibitors, compositions containing the same, methods for inhibiting calcium entry into electrically non-excitable cells with said VG-selective inhibitors, methods for preventing proliferation of electrically non-excitable cells with said VG-selective inhibitors as well as methods of treating autoimmune diseases, preventing graft rejections, preventing apoptosis and treating cancer with the same.

2. Discussion of the Background

Cellular activation and proliferation are fundamental to myriad biologic processes. For example, appropriate activation of lymphocytes is the basis of immunity, while epithelial cell proliferation is required for wound healing. In other cases these same processes can be destructive. Inappropriate activation of lymphocytes produces autoimmune diseases while uncontrolled or dysregulated proliferation is the hallmark of cancer.

Recognition of the critical roles of cell activation and proliferation has spurred a quest to decipher the mechanisms regulating them in the hope of controlling them for therapeutic purposes. One of the earliest components of these regulatory mechanisms is an increase in the concentration of calcium within the cell. Virtually all of this increase is delivered to the cell interior, or cytosol, from the extracellular medium via calcium selective channels. To date there is no approach to the control of calcium entry in cells such as lymphocytes and epithelial cells that is applicable to the practice of medicine.

An increase in the cytosolic calcium concentration is so widespread and essential to cellular function that its regulation forms a dichotomous categorization of cell types. Cells in which calcium influx is regulated by electrical activity at the plasma membrane are called "electrically excitable" and are exemplified by neurons and muscle cells. The calcium channels in these cells are termed "voltage gated" (VG) because they are regulated primarily by the change in voltage across the plasma membrane. All other cells, including lymphocytes and epithelial cells, lack the type of electrical activity occurring in electrically excitable cells and so are named "electrically non-excitable". The calcium channels in these types of cell are also referred to as VG channels by the inventors. To understand this invention, it is necessary to know that $Ca^{2+}$ entry in these latter types of cells in conventionally believed to be conducted by non-voltage gated (NVG) channels.

Knowledge about voltage gated calcium channels in electrically excitable cells has been exploited profitably. Pharmacological modulation of these channels' function is tremendously important in the practice of medicine; for example, calcium channel blockers are in widespread use in the treatment of epilepsy, hypertension, and angina pectoris. Unfortunately, such intervention is not yet available for calcium channels in electrically non-excitable cells. This deficiency likely reflects the fact that the mechanism by which calcium entry occurs has not been clearly identified.

SUMMARY OF THE INVENTION

Accordingly, one object of the present invention is to provide methods for screening for voltage gated (VG)-selective inhibitors.

A second object of the present invention is to provide novel VG-selective inhibitors.

A third object of the present invention is to provide novel compositions containing VG-selective inhibitors.

A fourth object of the present invention is to provide methods for inhibiting calcium entry into electrically non-excitable cells with said VG-selective inhibitors.

A fifth object of the present invention is to provide methods for preventing proliferation of electrically non-excitable cells, with said VG-selective inhibitors.

A sixth object of the present invention is to provide methods of treating autoimmune diseases, with said VG-selective inhibitors.

A seventh object of the present invention is to provide methods for preventing graft rejections, with said VG-selective inhibitors.

An eighth object of the present invention is to provide methods for preventing apoptosis.

A ninth object of the present invention is to provide methods for treating cancer.

The present inventors have now identified the current which mediates receptor-initiated increase in intracellular calcium in electrically non-excitable cells such as T cells: a novel $Ca^{2+}$ voltage gated (VG) current and an electrically passive, non-voltage gated current. The inventors have discovered that identification of the proper current, and hence channel, in non-excitable cells is critical for the development of new pharmacologic agents that inhibit activation and proliferation of electrically non-excitable cells. The present inventors have now discovered that activation-associated entry of $Ca^{2+}$ is mediated by the VG $Ca^{2+}$ current, with properties similar to T type, low voltage activated $Ca^{2+}$ currents, and that the non-voltage gated current is not required for activation-linked $Ca^{2+}$ entry. Based on their discovery the above objects of the present invention were achieved.

the addition of 300 nM thapsigargin. Voltage steps were 50 ms long and were applied at 2 s intervals. This cell is representative of 10 cells tested. (B) an inward current is shown that develops after thapsigargin treatment of a Jurkat cell with the membrane potential maintained at −6 mV in the perforated patch configuration. The current appeared 2 min after addition of 300 nM of thapsigargin and was blocked by 1 mM $NiCl_2$ added 10 min after the appearance of the current. Data points are 50 ms averages of the current obtained at 5 s intervals. This cell is representative of more than 30 cells tested. (C) The current-voltage relation for the current demonstrated in panel B. Continuous voltage ramps from −60 mV to 30 mV over 250 ms were applied to Jurkat cells in the perforated patch configuration. Membrane currents obtained from three ramps before addition of 300 nM thapsigargin were averaged and subtracted from the corresponding average obtained after the appearance of the current to obtain the net inward current. This trace is representative of the results in 10 cells. Traces are representative of 3 similar experiments.

Figure 3A:
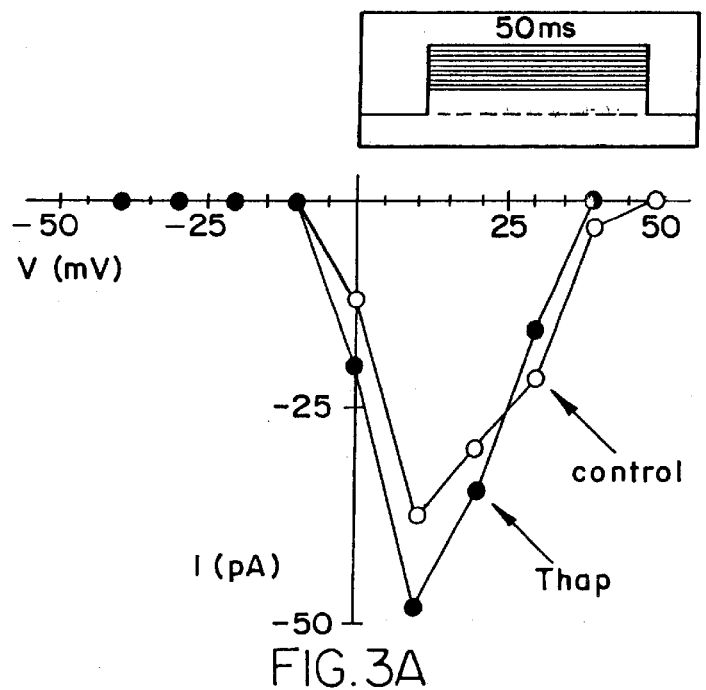
FIGS. 3A–C are graphs depicting how thapsigargin enhances both the VG and NVG currents. (A) the peak inward currents are shown for Jurkat cell in the perforated patch configuration using the voltage protocol in the inset with 10 mV steps from a holding potential of −90 mV to potentials from −40 to 50 mV. Peak inward $Ca^{2+}$ currents were measured before (open circles) and after (filled circles)
Figure 4A:
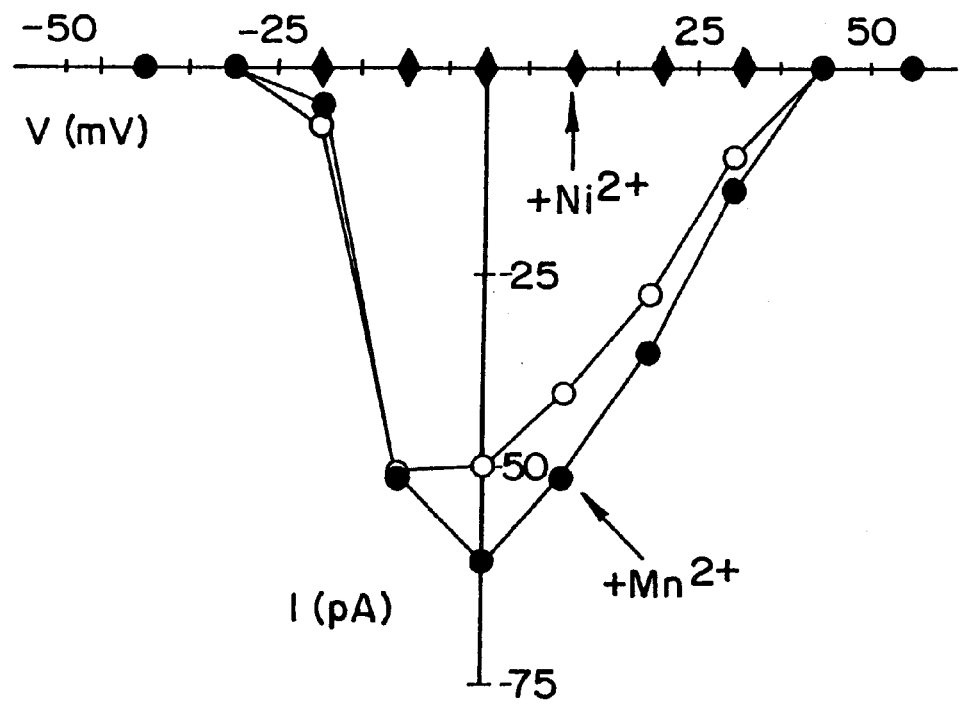
Figure 4B:
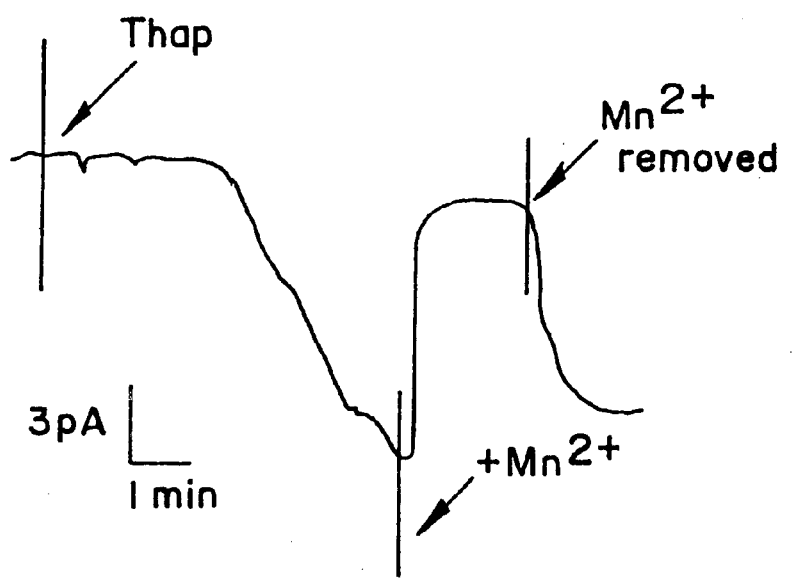

FIGS. 4A–B are graphs depicting that $Mn^{2+}$ does not inhibit the VG current but reversibly blocks the NVG current. (A) The peak inward current was measured using the voltage clamp protocol in FIG. 3A. The current-voltage relations were determined before (open circles) and after addition of 300 μM $MnCl_2$ to the bath solution (+$Mn^{2+}$, filled circles). Finally 1 mM $NiCl_2$ was added and the current-voltage-relation was determined again (+$Ni^{2+}$, ♦). This cell is representative of 4 experiments. (B) the NVG current was monitored with the membrane potential held constant at −60 mV. At the time indicated, 300 nM thapsigargin (Thap) was added followed by addition of 300 μM $MnCl_2$ ($MN^{2+}$) and subsequent washout of the $MnCl_2$ ($MN^{2+}$ removed). The trace is representative of 5 similar experiments.

Figure 5A:
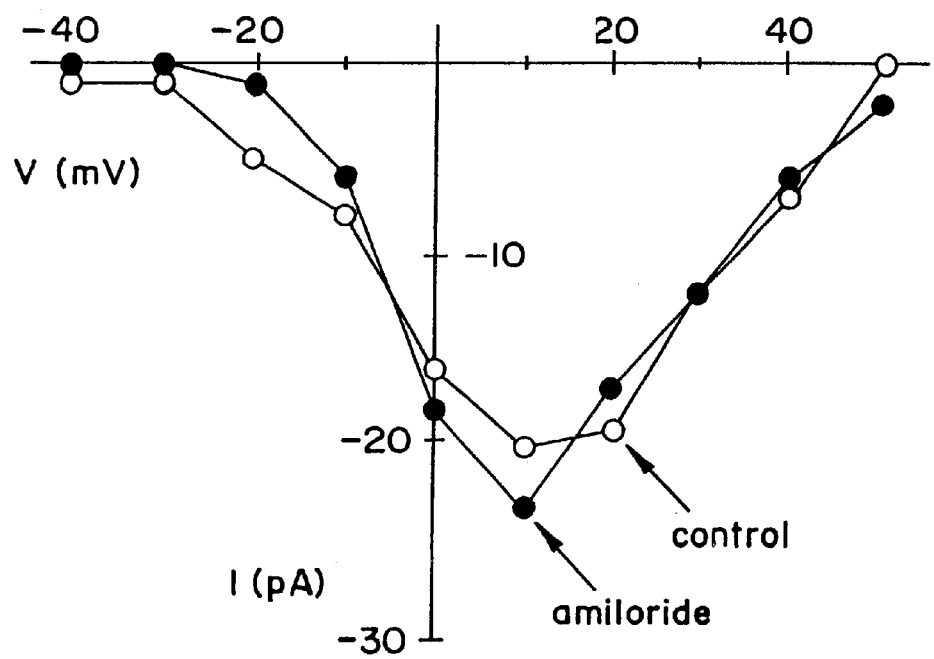
Figure 5B:
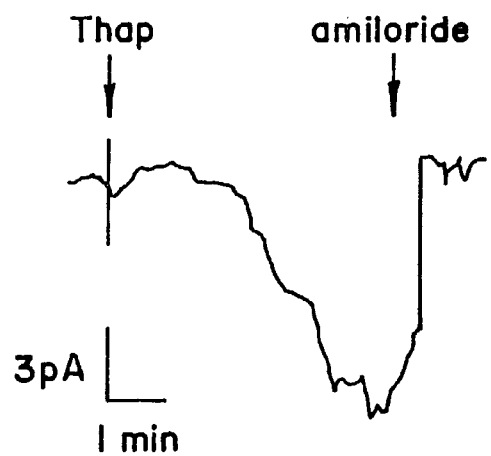

FIGS. 5A–B are graphs depicting that amiloride does not decrease the VG $Ca^{2+}$ current. (A) The peak inward VG $Ca^{2+}$ currents were measured as described in the legend to FIG. 3A. The current-voltage relations are shown before (control, pen circles) and after (+amiloride, filled circles) the addition of 100 μM amiloride to the bath solution. This cell is representative of 4 similar experiments. (B) The NVG current was activated by the addition of 300 nM thapsigargin (Thap) at the time indicated to a Jurkat cell with the membrane potential maintained at −60 mV. Amiloride (100 μM) added to the bath solution at the time indicated completely inhibited the inward current. This cell is representative of 4 similar experiments.

Figure 3B:
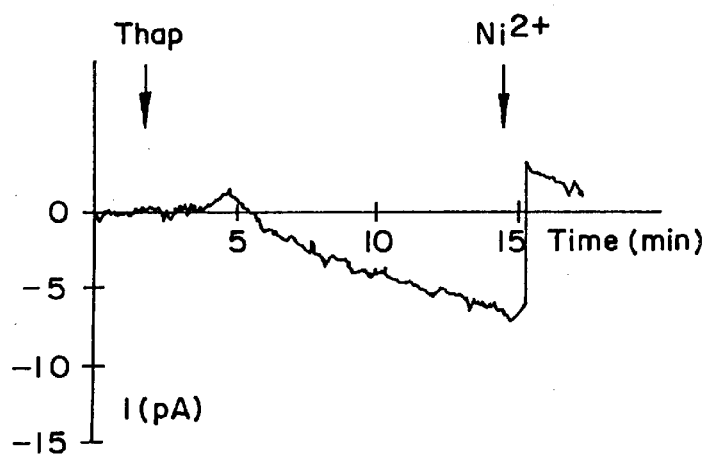
Figure 6A:
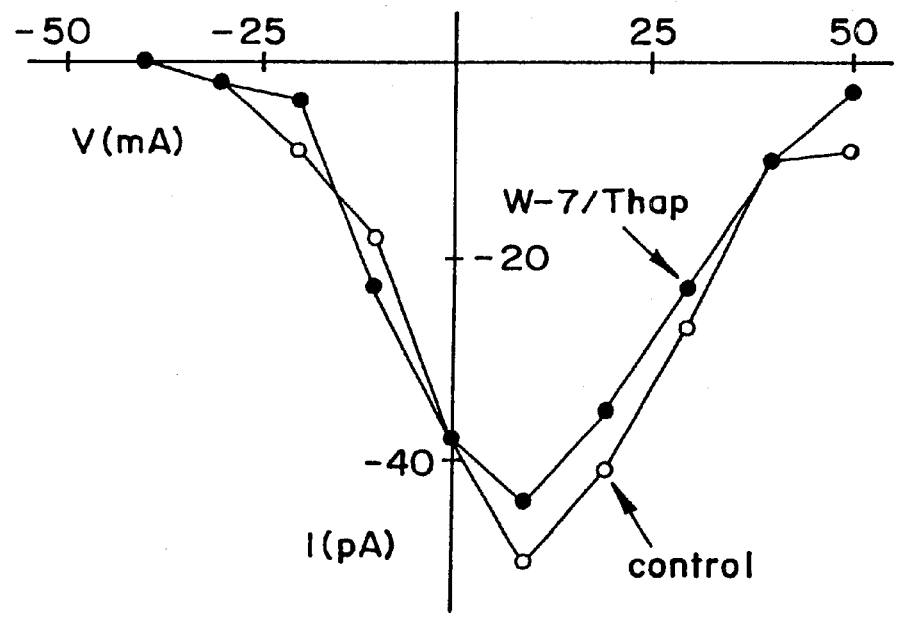
Figure 6B:
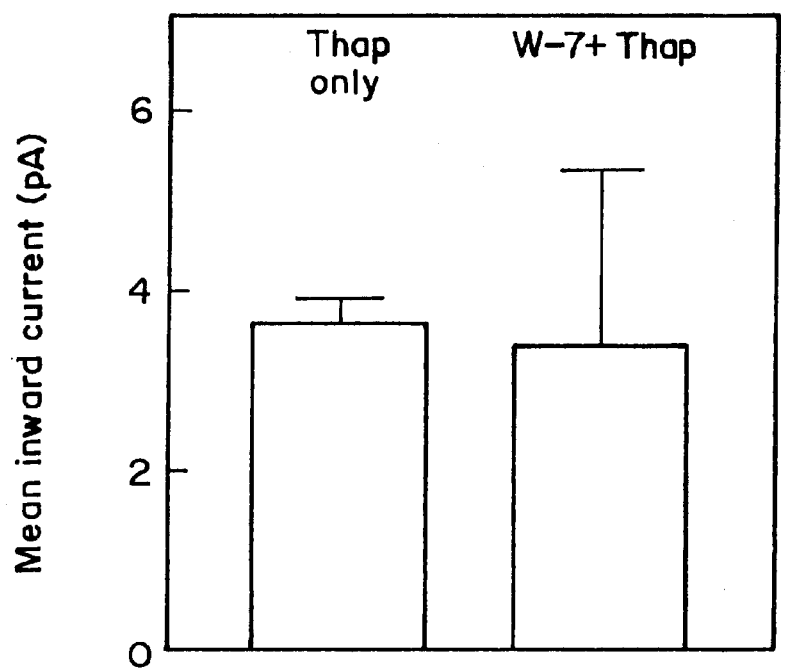

FIGS. 6A–B depict that CaM inhibitors block augmentation of the VG current by thapsigargin but have no effect on the thapsigargin-induced NVG current. (A) Current-voltage relations for the VG $Ca^{2+}$ current in a Jurkat cell before (control, open circles) and after addition of 30 μM W-7 and subsequent addition of 300 nM thapsigargin (+W-7/Thap, filled circles). Note that the thapsigargin-induced increase in the VG $Ca^{2+}$ current shown in FIG. 3A does not occur with prior addition of the CaM inhibitor, W-7. The data are representative of 5 similar experiments. (B) The NVG current was measured with the membrane potential held at −60 mV as shown in FIG. 3B. The peak inward current was measured after addition of 300 nM thapsigargin (Thap only) or 30 μM W-7 followed by 300 nM thapsigargin (W-7+Thap). Each bar represents the mean (±1SD) for 4 Jurkat cells.

Figure 7A:
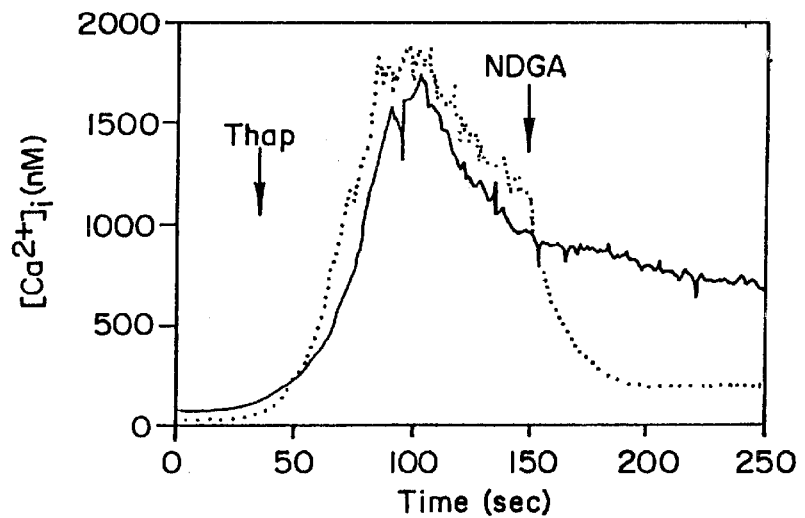
Figure 7B:
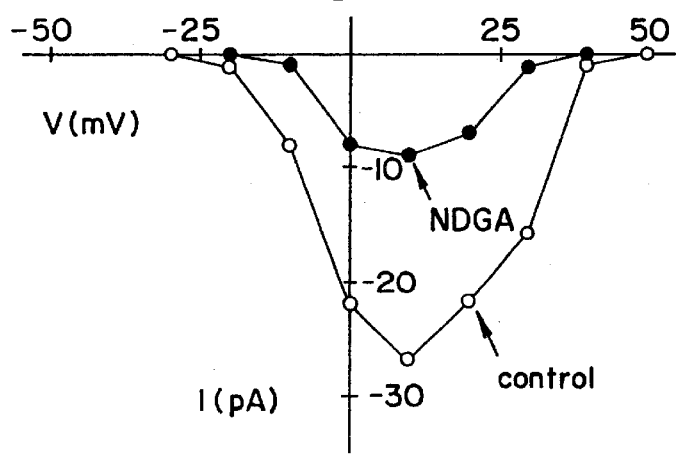
Figure 7C:
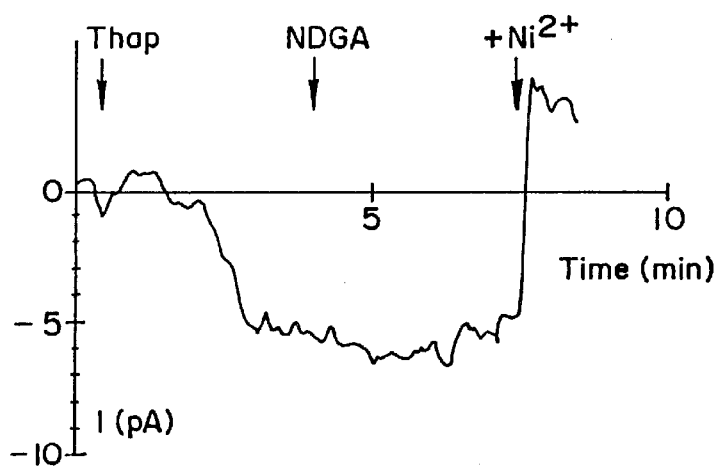

FIGS. 7A–C NDGA blocks thapsigargin-stimulated $Ca^{2+}$ entry as determined by $Ca^{2+}$-sensitive dyes and eliminates the VG current but does not block the NVG current. (A) $[Ca^{2+}]_i$ was measured with indo-1 as described previously (Haverstaick and Gray, Mol. Biol. Cell (1993) 4:173). For both traces, 300 nM thapsigargin (Thap) was added at the time indicated. NDGA (10 μM) was added at the indicated time to the cell suspension (dashed trace). Each trace is the mean of three experiments. (B) The current-voltage relation for the VG $Ca^{2+}$ current was measured as described in the legend to FIG. 3A both before (control, open circles) and after (+NDGA, filled circles) addition of 10 μM NDGA. (C) The NVG current was measured as described in the legend to FIG. 3B. Ten μM NDGA (+NDGA) had no effect on the inward current although it was eliminated by 1 mM $NiCl_2$ (+$Ni^{2+}$). This experiment is representative of 4 similar experiments.

Figure 8:
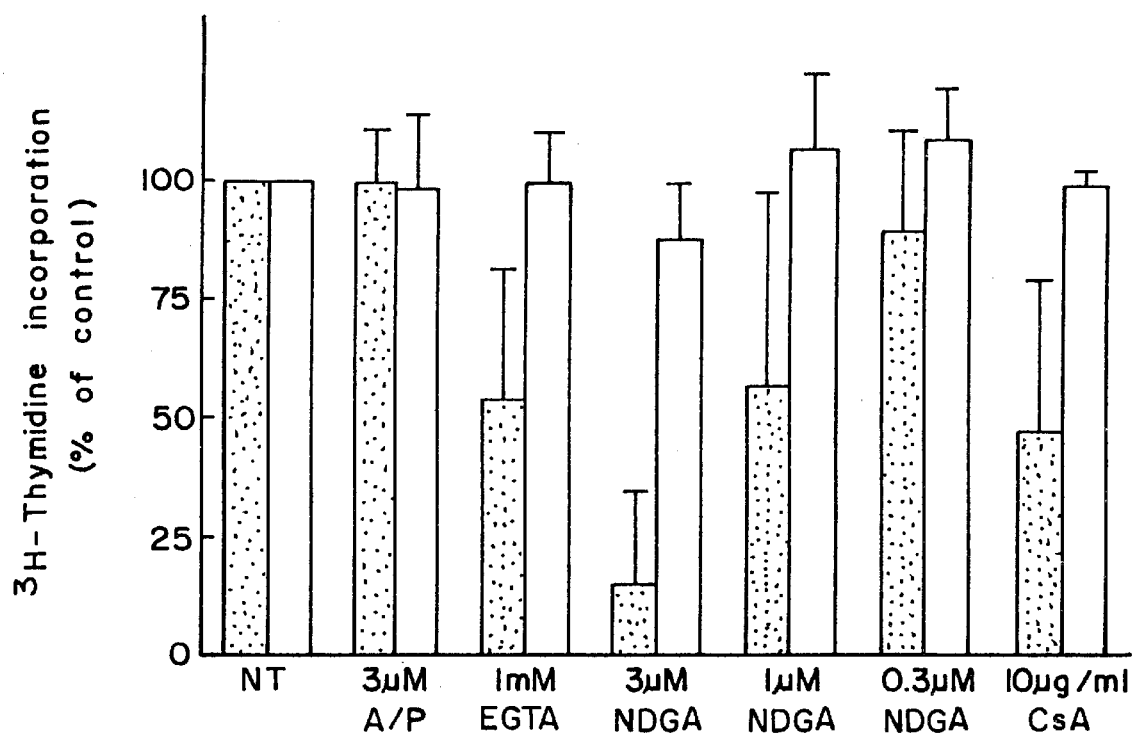

FIG. 8 is a bar graph depicting the inhibition of human PBMC proliferation by NDGA. Human peripheral blood mononuclear cells were stimulated in a $Ca^{2+}$-dependent manner (filled bars) or in a $Ca^{2+}$-independent manner (open bars) as described in Material and Methods. Proliferation was measured by $^3$H-thymidine incorporation during the final 16-hour or the 48-hour experiment and is shown as percent of control, untreated cells (NT). Treatments listed below bars were present for 15 minutes prior to stimulation and during the 1 hour stimulation with PHA/PDB. A/P refers to cells treated with 3 μM ASA and 3 μM phenidone. Bars represent the mean±1SD for 5 experiments (NT, EGTA, NDGA) or 4 experiments (A/P, CsA)

Figure 9:
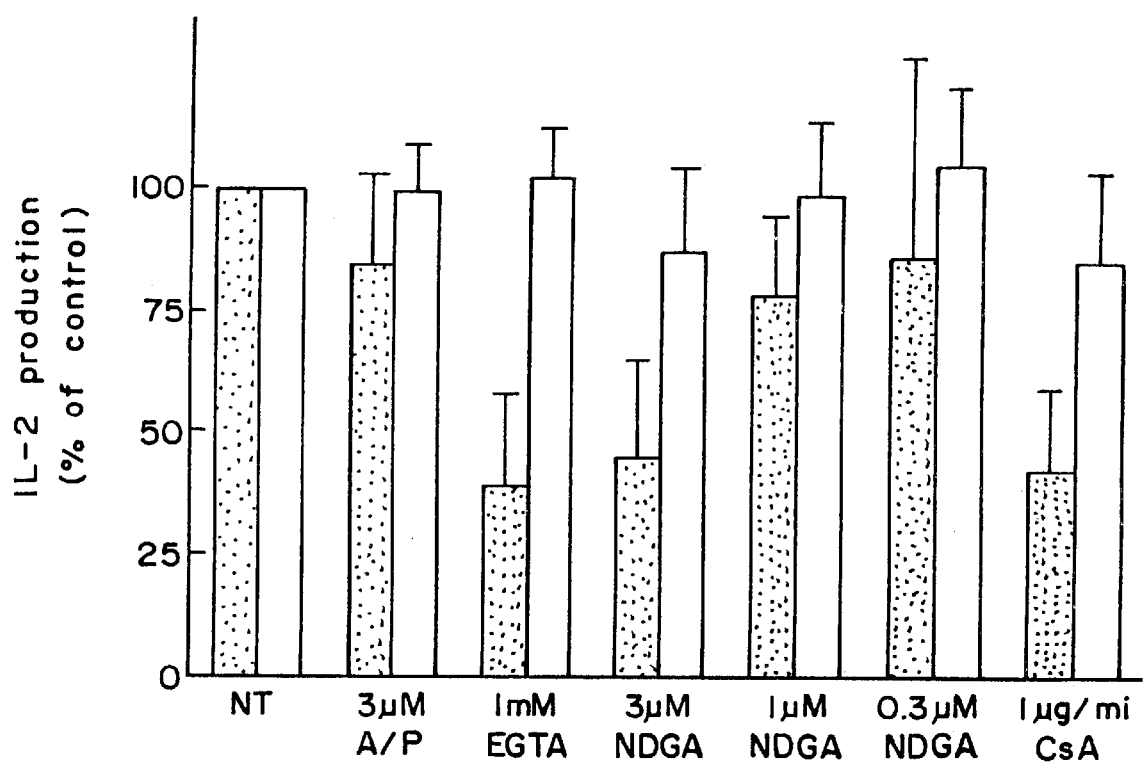

FIG. 9 is a bar graph depicting the inhibition of IL-2 production by NDGA. Jurkat cells were stimulated in either a $Ca^{2+}$-dependent manner (filled bars) or in a $Ca^{2+}$-independent manner (open bars) and IL-2 production was measured as outlined in Material and Methods. Treatments listed were present for the 15 minutes prior to stimulation and were present throughout the 2 hours stimulation period. Control IL-2 production ranged from 15–25 U/ml for the $Ca^{2+}$-dependent and 20–40 μ/ml for the $Ca^{2+}$-independent stimulus regimen. A/P refers to cells treated with 3 μM ASA and 3 μM phenidone. Bars represent the mean±1SD for 4 experiments (NT, EGTA, NDGA) or 3 experiments (A/P CsA).

DETAILED DESCRIPTION OF THE PREFERRED EMBODIMENTS

The method of the present invention comprises administering to an electrically non-excitable cell an amount of a VG-selective inhibitor which is sufficient to decrease the free calcium concentration in the cytosol.

VG-selective inhibitors are defined herein as compounds which inhibit the $Ca^{2+}$ VG current but which do not effect the non-voltage gated current. Compounds which are VG-selective inhibitors can be screened for by:

(i) incubating a non-electrically excitable cell with (1) a dye which has acid groups which can coordinate $Ca^{2+}$ and which undergoes a spectral shift when coordinated to $Ca^{2+}$ and (2) a compound with unknown effect;

(ii) stimulating $Ca^{2+}$ influx into the cell; and (iii) monitoring the spectral characteristics of the dye in the non-electrically excitable cells. These spectral characteristics will change as calcium is bound to the dye. Because calcium will bind to (be coordinated by) the dye in proportion to the concentration of calcium in the cytosol, the change in spectral characteristics of the dye will be a measure of the calcium concentration within the cytosol.

If the compound is a VG-selective inhibitor than the absorbance or fluorescent emission of the uncoordinated dye ($A_1$) will be different than the absorbance or fluorescent emission of the $Ca^{2+}$-coordinated dye ($A_2$) because the VG-selective inhibitor will have suppressed calcium entry into the cytosol.

Compounds that are VG-selective inhibitors may also be screened for by:

(i) establishing an electrical connection with a non-electrically excitable cell in such a fashion as to measure the electrical changes occurring at the plasma membrane (This is typified, but not limited to, the well described patch clamp technique);

(ii) stimulating $Ca^{2+}$ influx into the cell; and (iii) monitoring the inward current attributable to $Ca^{2+}$, entry or monitoring currents or changes in membrane potential which are likely due to $Ca^{2+}$ entry such as activation of $Ca^{2+}$-activated $K^+$ currents.

If the compound is a VG-selective inhibitor than electrical changes due primarily or secondarily to activation of the VG $Ca^{2+}$ current will not occur or will be modified in some manner predictable by electrophysiological concepts.

Electrically non-excitable cells as used herein are any cells which are not electrically excitable, that is, cells in which calcium influx is not initiated by electrical activity at the plasma membrane. Electrically non-excitable cells contain VG or "receptor operated" calcium channels.

Suitable electrically non-excitable cells useful in accordance with the present invention include any cell which requires the entry of $Ca^{2+}$ for activation or proliferation but which does not initiate entry of $Ca^{2+}$ by an electrical action potential such as occurs in neurons. Non-excitable cells include lymphocytes, and other formed elements of the blood epithelial cells, connective tissue cells and secretory cells including glandular cells. Particularly preferred electrically non-excitable cells for the purpose of screening include Jurkat cells (a lymphocyte), MDA-468 (a breast cancer cell line), PC-3 (a prostrate cancer cell line, or any cell type or cell line which is electrically non-excitable. The cells lines mentioned above are available from the American Type Culture Correction, Rockville, Md.

Suitable dyes useful in accordance with the present invention include any dye which can coordinate $Ca^{2+}$ and which undergo a spectral shift when coordinated to $Ca^{2+}$. Preferably hydrophobic dyes which are permeable to the cell membrane are used, although other dyes can be used. Particularly preferably hydrophobic dyes which contain ester groups are used. After such dyes permeate the cell, the ester groups are cleaved, trapping the dye in the cell. Preferred dyes include indo-1, fura-2, fluo-3, calcium green, green-2, rhod-2, calcium orange, calcium crimson and fura red. These dyes are available from, for example, Molecular Probes, Eugene, WA or CALBIOCHEM, LaJolla, Calif. These dyes have the following absorbances and emissions.

| DYE | LOW CALCIUM | | | HIGH CALCIUM | | |
|---|---|---|---|---|---|---|
| | ABS | {ex} | EM | ABS | {ex} | EM |
| indo-1 | 346 | 33 | 475 | 330 | 33 | 408 |
| fura-2 | 362 | 27 | 512 | 335 | 27 | 505 |
| fluo-3 | 506 | 78 | 526 | 506 | 83 | 526 |
| calcium green | 506 | 63 | 531 | 506 | 93 | 531 |
| quin-2 | 352 | 5 | 492 | 332 | 5 | 491 |
| rhod-2[a] | 556 | 80 | 576 | 553 | 80 | 576 |
| calcium orange | 554 | 80 | 575 | 555 | 80 | 576 |
| calcium crimson[a] | 588 | 108 | 611 | 588 | 108 | 611 |
| fura red | 472 | 29 | 645 | 436 | 41 | 640 |

"ABS" is the wavelength maximally absorbed while "EM" is the wavelength maximally emitted. Both values are in nm. {ex} in the extinction coefficient $\times 10^{-3}$.

[a]These dyes have a markedly increased emission at high calcium concentrations due to an increase in the quantum yield.

The absorbance of the dye can be measured using a fluorometer as described in Grynkiewiz et al, 1985, *J. Biol. Chem.* 260:3440–3450; Gray et al, 1987, *J. Immunol.* 138:63–69; Gray et al, 1987, *Cell* 50:119–127; Gray et al, 1988, *J. Immunol.* 141:2424–2430; Gray et al, 1988, *J. Exp. Med.* 167:1963–1968; and Gray et al, 1989, *J. Immunol.* 142:1631–1638. Preferably, the uncoordinated dye absorbs at a wavelength which is greater than 20 nm from that of the coordinated dye.

Calcium influx into the cell can be suitably stimulated using either (1) a physiological ligand or (2) an endoplasmic reticulum (ER) ATPase inhibitor. Preferably, a physiological ligand is used to stimulate calcium influx into the cell.

A physiological ligand as used herein is a ligand which binds to a receptor on a non-electrically excitable cell and stimulates $Ca^{2+}$ influx into the cell. Depending on the non-electrically excitable cell used, these ligands will vary. For example, suitable ligands for use with Jurkat cells include antibodies to the T cell receptor for antigen, e.g., OKT3. Suitable ligands for use with MDA 468 cells include epidermal growth factor or transforming growth factor. Suitable ligands for use with PC-3 cells include epidermal growth factor or purinergic agonists such as adenosine. These are reviewed in Carpenter and Cohen, 1990, *J. Biol. Chem.* 265:7709–7712; Crabtree and Clipstone, 1994. *Annu. Rev. Biochem.* 63:1045–1083; and Gardner, P. 1989. *Cell* 59:15–20. These reagents are available from several suppliers such as Sigma, CALBIOCHEM, Research Diagnostics (Flanders, N.Y.), Chemicon (Temecula, Calif.).

An ER ATPase inhibitor as used herein is any compound which stimulates the release of $Ca^{2+}$ from the ER into the cytoplasm, which in turn activates calmodulin, which in turn activates $Ca^{2+}$ entry into the cell (for a review of ER ATPase inhibitors, see Thastrup, O., Agents & Actions (1990) 29:8–15; Inesi and Sagara. Archives of Biochem & Biophy. (1992) 298:313–7; and Darby et al, Biological Signals (1993) 2:293–304. Preferred ER ATPase inhibitors include cyclopiazonic acid (available from Sigma, St. Louis Mo.) and thapsigargin (available from Sigma).

Using the above method, several classes of VG-selective inhibitors have been identified including phenothiazines, piperazines, dihydropyridines, phenylalkylamines, benzothiazepines, benzylisoquinolines and derivatives of N-(6-aminohexyl)-5-chloro-1-napthalenesulfonamide.

Suitable phenothiazine derivatives useful in accordance with the present invention include compounds of the formula (I):

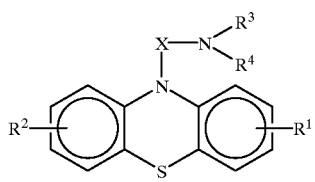

where $R^1$ and $R^2$ are each, independently, hydrogen, fluorine, bromine, chlorine, iodine or a $C_{1-4}$ alkyl; X is a straight or branched chain $C_{1-4}$ alkylene; and $R^3$ and $R^4$ are each, independently, hydrogen or a $C_{1-4}$ lower alkyl.

Preferred compound of the formula (I) include trifluoperazine, chlorpromazine, promethazine, promazine, acetopromazine, butaperazine, ethopropazine, fluphenazine, mesoridazine, methotrimeprazine, moricizine, nonachazine, perazine, perphenazine, pipothiazine, prochlorperazine, propericiazine, propiomazine, thiethylperazine, thioproperazine, thioridazine, triflupromazine, and trimeprazine. These compounds are generally available from Sigma (St. Louis Mo.) or Aldrich (Milwaukee Wis.).

These and other suitable phenothiazine derivatives can be synthesized using procedures known in the art. For example, trifluoperazine, N,N-dimethyl-2-(trifluoromethyl)-10H -phenothiazine-10-propanamine, is commercially available, for example from Sigma (St. Louis Mo.). Alternatively, it can be synthesized as described in British patent 813,861. Chlorpromazine, 2-chloro-10-[3-dimethylaminopropyl]-phenothiazine, is commercially available, for example from Sigma. Alternatively, it can be synthesized as described in U.S. Pat. No. 2,645,640. Promethazine, N,N,α-trimethyl-10H -phenothiazine-10-ethanamine, is commercially available, for example from St. Louis Mo. Alternatively, it can be synthesized as described in U.S. Pat. No. 2,530,451.

Suitable piperazines derivatives useful in accordance with the present invention include compounds of the formula (II):

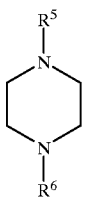

where $R^3$ and $R^4$ are each, independently, $C_{6-12}$ aryl or $C_{1-6}$alkyl($C_{6-12}$)aryl. Preferred piperazines include diphenylpiperizine and (diphenylbutyl)piperidine. These and other suitable piperazines derivatives can be synthesized as described by Saxena et al, J. Med. Chem. (1990) 33:2970–6; Glennon et al, J. Med. Chem. (1991) 34:3360–5; Shimazaki et al, Lipids (1991) 26:1175–8; Deutsch et al, Euro. J. Pharm. (1992) 220:173–80; Nikolova et al, Farmaco (1993) 48:459–72; Lamouri et al, J. Med. Chem. (1993) 36:990–1000; Sladowska H., Farmaco (1993) 48:77–84; Naylor et al, J. Med. Chem. (1993) 36:2075–83; Hayashi et al, Chem. & Pharm. Bull. (1993) 41:1091–9; Elmaleh et al, Nuclear Medicine & Biology (1993) 20:427–33; Carceller et al, J. Med. Chem. (1993) 36:2984–97; van Steen et al, J. Med. Chem. (1993) 36:2751–60; Romero et al. J. Med. Chem. (1994) 37:999–1014; Reitz et al. J. Med. Chem. (1994) 37:1060–2; Mokrosz et al, J. Med. Chem. (1994) 37:2754–60; van Steen et al, J. Med. Chem. (1994) 37:2761–73; Perrone et al, J. Med. Chem. (1994) 37:99–104; Fukushi et al, Chem. & Pharm. Bull. (1994) 42:541–50; and Fukushi et al, Chem. & Pharm. Bull. (1994) 42:551–9.

Suitable dihydropyridine derivatives useful in accordance with the present invention include compounds of the formula (III):

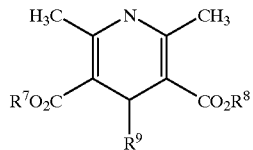

where $R^7$ and $R^8$ are each, independently, a $C_{1-6}$ alkyl, —$(CH_2)_n XR^{10}$ where n is 1, 2 or 3; X is O, NH or $NR^{11}$; and $R^{10}$ and $R^{11}$ are each, independently, hydrogen, $C_{1-6}$ alkyl or $C_{6-10}$ aryl; and $R^9$ is an unsubstituted or mono or di-substituted $C_{6-12}$ aryl or $C_{6-12}$ hetereoaryl, suitable substituents including nitro, halo (—Cl, —F, —Br, or—I), or $C_{1-6}$ alkyl. Preferred compounds of the formula (iii) include amlodipine (Burges et al, Am. J. Cardiology (1994) 73:2A-9A), dicarbethoxydihydrocollidine (Kimmett et al, Can. J. Physiol. Pharm. (1994) 72:397–401), felodipine, isradipine, nicardipine, nifedipine, nimodipine, nisoldipine, and nitrendipine. These compounds are available from Aldrich and Sigma.

Suitable phenylalkylamines derivatives useful in accordance with the present invention include compounds of the formula (IV):

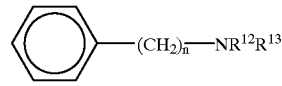

where n is an integer of from 1–6 and $R^{12}$ and $R^{13}$ are each independently, $C_{1-4}$ alkyl or hydrogen. Preferred phenylalkylamines include phenethylamine available from Aldrich.

Suitable benzothiazepine derivatives useful in accordance with the present invention include 1,5-benzothiazepine derivatives, especially those of the formula (V):

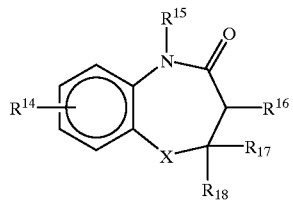

where $R^{14}$ is hydrogen, halogen, $C_{1-6}$alkyl, $C_{1-6}$alkoxy, $C_{6-12}$aryl, $C_{6-12}$aryl ($C_{1-6}$) alkyl, $C_{6-12}$aryl ($C_{1-6}$) alkoxy or $C_{6-12}$aryloxy;

X is O or S, $R^{15}$ is —$CH_nCO_2R^{19}$, —$CH_nCOR^{19}$, —$CH_nCONR^{20}R^{21}$ or —$CH_nNR^{20}R^{21}$;

$R^{16}$ is —$OCOR^{19}$ or —$NHCONR^{20}R^{21}$;

$R^{17}$ to $R^{21}$ each, independently, are hydrogen, nitro, amino, $C_{1-6}$alkyl, $C_{1-6}$alkylamino, hydroxy, $C_{1-6}$alkoxy, $C_{6-12}$aryl, $C_{1-6}$alkyl ($C_{6-12}$)aryl, halo ($C_{6-12}$) aryl or $C_{1-6}$alkoxy($C_{6-12}$)aryl, in addition $R^{20}$ and $R^{21}$ taken together with the nitrogen to which they are attached may form a cyclic amino group.

These and other suitable benzothiazepine derivatives can be synthesized as described in EP 0 609 031, WO 94/01421, FR 2,623,192 and as described by Giannotti et al, J. Med. Chem. (1991) 34:1356–62; Inoue et al, J. Med. Chem.

(1991) 34:675–87; Li et al, Drug Design & Discovery (1993) 10:331–42; Garofalo et al, Farmaco (1993) 48:275–83; Ambrogi et al, Farmaco (1993) 48:665–76; Perioli et al, Farmaco (1994) 49:245–51; and Fiorini et al, J. Med. Chem. (1994) 37:1427–38.

Suitable benzylisoquinoline derivatives useful in accordance with the present invention include compounds of the formula (VI):

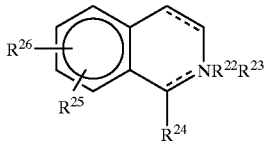

where — — — represents a double or single bond; $R^{22}$ and $R^{23}$ are each, independently, hydrogen or $C_{1-6}$ alkyl; $R^{24}$ is hydrogen, $C_{6-1}$ alkyl, —$COOR^{27}$, —$CONHR^{27}$ or —$COR^{27}$ where $R^{27}$ is hydrogen or $C_{1-6}$ alkyl; $R^{25}$ and $R^{26}$ are each, independently, hydrogen, halogen, —$PO_3H_2$, —$(CH_2)_n PO_3H_2$ where n is an integer of 1 to 6, $C_{1-6}$ alkyl or $C_{1-6}$ alkoxy.

These and other suitable benzylisoquinoline derivatives can be synthesized as described by Bembenek et al, J. Med. Chem. (1990) 33:147–52; Ortwine et al, J. Med. Chem. (1992) 35:1345–70; Russell et al, J. Med. Chem. (1992) 35:2025–33; Santagati et al, Farmaco (1993) 48:21–30; Janin et al, Chem. & Pharm. Bull. (1994) 42:892–5.

Alternatively, a benzoisoquinoline derivative of the formula (VII) can be used:

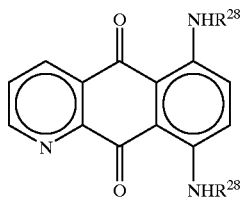

where $R^{28}$ is hydrogen, $C_{1-6}$ alkyl, —$(CH_2)_x R^{29}$ where x is an integer of 1 to 6 and $R^{29}$ is hydrogen, morpholino, piperidino, —$O(CH_2)_y OH$, —$O(CH_2)_y CH_3$, —$NH(CH_2)_y CH_3$, —$NH(CH_2)_y OH$, —$NH(CH_2)_y NH_2$, —$NHCOR^{30}$, —$N[(CH_2)_y CH_3]$, or —$NCO_2 R^{30}$ where y is an integer between 0 and 6 and $R^{30}$ is hydrogen or $C_{1-6}$ alkyl. These and other suitable benzylisoquinoline derivatives can be synthesized as described by Krapcho et al, J. Med. Chem. (1994) 37:828–37.

Other suitable benzoisoquinoline derivatives useful in the present invention include those of the formula (VIII):

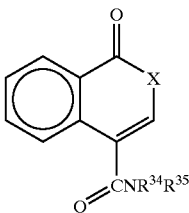

where X is O or $NR^{33}$; $R^{33}$ is $C_{1-6}$ alkyl; and $R^{34}$ and $R^{35}$ are each, independently, hydrogen, $C_{1-6}$ alkyl, $C_{1-6}$ alkylene, or $C_{1-6}$ alkylamine; or $R^{34}$ and $R^{35}$ jointly form a 5- or 6-membered alkyl ring of which any of the carbon atoms may be substituted with oxygen or nitrogen. Preferred 5- and 6-membered rings include morpholino, piperidino, pyrolidino and N-methylpiperazino. These and other suitable benzylisoquinoline derivatives can be synthesized as described by Santagati et al, Il Farmaco (1993) 48:21–30.

Other suitable benzoisoquinolines useful in accordance with the present invention include those of the formula (IX):

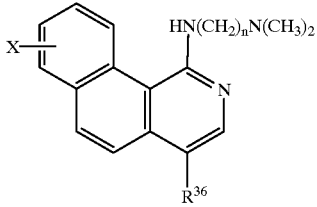

where n is an integer from 1 to 5; X is a hydrogen, halogen, $C_{1-6}$ alkyl, $C_{1-6}$ alkylene, $C_{1-6}$ alkoxy or hydroxy and $R^{36}$ is hydrogen or $C_{1-6}$ alkyl. These and other suitable benzylisoquinoline derivatives can be synthesized as described by Janin et al, Chem. Pharm, Bull. (1994) 42:892–95.

Suitable omega-(arylsulfonamide)-alkylamine derivatives useful in accordance with the present invention include compounds of the formula (X):

where $R^{31}$ is an amino group or an acylated amino group, $R^{32}$ is a halonaphthyl group and n represent an integer of 5–8, and salts thereof. These and other suitable omega-(arylsulfonamide)-alkylamine derivatives are described in GB 1473433, JP 52100439, Hart et al, Methods in Enzymology (1983), 102 (Horm. Action, Part G):195. Preferred omega-(arylsulfonamide)-alkylamine derivatives useful in accordance with the present invention include N-(6-aminohexyl)-5-chloro-1-naphthalenesulfonamide (available from Sigma).

Nordihydroguaiaretic acid (NDGA) can also be used as a VG-selective inhibitor. NDGA, 4,4'-(2,3-dimethyl-1,4-butanediyl)bis[1,2-benzenediol], is commercially available, for example, from Sigma. Alternatively, NDGA can be synthesized as described in U.S. Pat. No. 2,644,822.

Tetrandine, 6,6',7,12-tetramethoxy-2,2'-dimethyl-baman, can also be used as a VG-selective inhibitor. Tetrandine is commercially available, for example, from Aldrich.

The VG-selective inhibitors of the present invention are useful for treating autoimmune diseases, graft rejections, graft versus host disease and cancer. Although the VG-selective inhibitors of the present invention can be used to treat any autoimmune disease, in preferred embodiments, the autoimmune diseases are rheumatoid arthritis, juvenile onset (insulin dependent) diabetes mellitus, autoimmune endocrinopathies such as thyroiditis and collagen vascular diseases such as systemic lupus erythematosus.

"Treating" means ameliorating a disease such that the condition of the patient improves or such that the progess of the disease is slowed. The beneficial effects of the VG-selective inhibitors of the present invention can be determined by monitoring an improvement in one or more symptoms; for example, by monitoring the decrease in proliferation (cancer), by monitoring the increased stablization of a graft in a patient (graft rejection), by monitoring the decreased joint swelling, inflammation and pain in a patient (rheumatoid arthritis), by monitoring the decrease in insulin requirement (juvenile onset diabetes mellitus), by monitoring the normalization of circulating levels of thyroid hormones in a patient (thyroiditis), by monitoring the decrease in nephritis (systemic lupus erythematosus), etc. Alternatively, the effects of the VG-selective inhibitors of the present invention can be monitored by comparing them against compounds conventionally used in the treatment of these diseases.

The VG-selective inhibitors of the present invention can be administered by conventional techniques, including by catheter, intravenously, subcutaneously, orally, endoscopically, intramuscularly as well as topically. The preferred mode of administration will, of course, depend on the intended use. Thus, for example, for autoimmune diseases the preferred mode of administration would be intravenously or orally.

The VG-selective inhibitors of the present invention can be administered in the form of any conventional composition suitable for the mode of administration being used. In general, the pharmaceutical compositions comprise an effective amount of an VG-selective inhibitor and a pharmaceutically acceptable carrier. Suitable ingredients and procedures for forming suitable pharmaceutical compositions are disclosed by Kirk-Othmer in *Encyclopedia of Chemical Technology*, 3rd ed., Wiley, N.Y., vol. 17, pp. 272–310 (1982), which is incorporated by reference. The exact dosage of VG-selective inhibitor to be administered will depend on the disease being treated and the size and condition of the patient. In general, the dose will be administered in a concentration and on a schedule that will expose the target tissue to a concentration of less than 50 to 100 $\mu M$. This concentration is equivalent to that which is effective for immunosuppression by cyclosporin A or calcium channel blockage in the treatment of hypertension by verapamil, nifedipine, nitrendipine or similar agents.

The VG-selective inhibitors of the present invention can also be coadministered with other compounds such as 3-methoxy-4-hydroxyphenylethanol, 3-methoxy-4-hydroxyphenylglycerol, amrinone, bepridil, bupropion, chlorcyclizine, cinnarizine, curcumin, cyclizine, datrolene, diethylcarbamazine, fendiline, flunarizine, fluphenazine, hydroxyzine, isradipine, lidoflazine, meclizine, mianserin, nicardipine, niflumic acid, perhexiline, pipemidic acid, prenylamine, quipazine, silymarin, tetramethylpyrazine, tetrandrine or trazodone. When combined with these compounds there are indications that synergy between the compounds increases the effects observed. Accordingly, when coadministered the dosage of VG-selective inhibitor can be suitably diminished while achieving the same effect.

Having generally described this invention, a further understanding can be obtained by reference to certain specific examples which are provided herein for purposes of illustration only and are not intended to be limiting unless otherwise specified.

EXAMPLES

Example 1

T Cell Suppression by Blockage of a Voltage Gated Calcium Channel

Materials and Methods
Cells and Reagents

The human T lymphocyte line Jurkat E6-1 was obtained from the ATCC (Rockville, Md.) and was maintained in RPMI-1640 (BioWhittaker, Walkersville, Md.) supplemented with glutamine and 5% fetal bovine serum (FBS). The murine IL-2-sensitive cell line CT-EV was a generous gift from Dr. William Paul. Ficoll-Hypaque density gradient centrifugation was used to isolate peripheral mononuclear cells from human blood obtained from healthy donors. Cells were maintained in a humidified incubator with 5% $CO_2$ at 37° C. BAPTA, indo-1/AM and fluo-3/AM were obtained from Molecular Probes (Eugene, Oreg.). Nordihydroguaiaretic acid was obtained from Aldrich (Milwaukee, Wis.) and W-7 from Calbiochem (San Diego, Calif.). All other reagents were obtained form Sigma (St. Louis, Mo.) and were dissolved in DMSO, with the exceptions of $NiCl_2$ and $MnCl_2$ which were dissolved in buffer A or bath solution. Addition of DMSO alone had no effect in experiments.

Measurement of $[Ca^{2+}]_i$ with Indo-1

Lymphocytes were suspended in culture medium at 37° C. for 1 h in the presence of 1 $\mu M$ of the $Ca^{2+}$ indicator dye indo-1 /AM. Cells were washed twice in buffer A (140 mM NaCl, 3 mM KCl, 1 mM $CaCl_2$, 1 mM $MgCl_2$, 0.1% D-glucose, 1% FBS, 10 mM HEPES, pH 7.4) and were suspended at a final concentration of $1 \times 10^6$ cells/ml in buffer A. The excitation wavelength was 340 nm and emission was monitored at 398 nm in an SLM 8000 spectrofluorometer (SLM/Aminco, Urbana, Ill.), with the temperature maintained at 37° C. Data are plotted as relative fluorescence intensity at 398 nm as a measure of $[Ca^{2+}]_i$. For FIG. 7, indo-1 emission was monitored at 398 nm and 480 nm and $[Ca^{2+}]_i$ was determined as described previously (Gray et al, J. Immunol (1987) 138:63; Haverstick et al, Mol. Biol. Cell (1993) 4:173).

Manganese Quench of Indo-1 Fluorescence

Jurkat cells were loaded with indo-1/AM as described above. The excitation wavelength was 340 nm and emission was measured at 441 nm. The fluorescence of indo-1 at 441 nm is insensitive to changes in $[Ca^{2+}]_i$ (Sage et al, Biochem. J. (1989) 258:923) and is plotted as relative fluorescence intensity.

Measurement of $[Ca^{2+}]_i$ with Fluo-3

Because amiloride interferes with the fluorescence of indo-1 (Wacholtz et al, J. Immunol. (1992) 149:1912), fluo-3 was used to monitor $[Ca^{2+}]_i$ in the presence of amiloride. Jurkat cells were suspended in culture medium at 37° C. for 1 h in the presence of 1 $\mu M$ fluo-3/AM and 1 mM probenecid to decrease dye leakage (DiVirgilio et al, Methods Cell Biol. (1989) 31:453). After two washes in buffer A, cells were suspended at a concentration of $1 \times 10^6$ cells/ml in buffer A with 1 mM probenecid and were maintained in a cuvette at 37° C. The excitation wavelength was 506 nm and the emission was monitored at 526 nm. Data are presented sa relative fluorescence intensity at 526 nm.

Electrophysiology

All recordings were performed using the perforated patch method (Horn et al, J. Gen. Physiol. (1988) 92:145) of the gigaseal patch clamp technique (Hammil et al, Pflugers Arch (1981) 391:85) with microelectrodes of 5–10 megohm series resistance. In all solutions for voltage clamp, $K^+$ was replaced with $Cs^+$ to block outward $K^+$ currents (Fox et al, J. Physiol. (Lond.) (1987) 392:149). The bath solution contained (in mM): NaCl, 155; CsCl, 4.5; $CaCl_2$, 2; $MgCl_2$, 1; D-glucose, 5; HEPES, 10 (pH 7.4 with NaOH). The pipette solution contained (in mM): CsCl, 55; Cesium methanesulfonate, 70; $CaCl_2$, 1; $MgCl_2$, 7; HEPES, 10 (pH 7.3 with NaOH). Nystatin was made as a stock solution of 6 mg/100 $\mu l$ DMSO, and 2 $\mu l$ of the stock was added to 1 ml of the pipette solution for use. Both pipette and bath solutions were 290–300 mOsm. Experiments were performed on cells at room temperature using the Axopatch-1D patch clamp (Axon Instruments, Foster City, Calif.) after correction of junction potentials and leak subtraction. Records were low-pass filtered at 500 Hz, and the data were collected, stored and analyzed using the pClamp software program (Axon Instruments). For the non-voltage gated current traces, data is presented either as the tracing from a chart recorder or from the digital data in which the current was measured at 5 second intervals and plotted as individual points.

Lymphocyte Proliferation

Human PBMC were isolated from peripheral blood obtained from healthy donors. Cells were washed twice and were placed in triplicate wells at a concentration of $1 \times 10^5$ cells/ml in serum-free RPMI-1640 supplemented with 100 U of both penicillin and streptomycin. Drug treatments were added 15 minutes before stimulation of the cells and were present throughout the 1 hour stimulation period. Stimulation by mitogen (1 $\mu$g/ml PHA) in combination with 10 nM phorbol dibutyrate (PDB) was carried out for 1 hour at 37° C. Cells were subsequently washed 3 times with RPMI and were resuspended at a concentration of $1 \times 10^5$ cells/ml in RPMI-1640 supplemented with 5% FBS and 100 U/ml of penicillin and 100 $\mu$g/ml streptomycin. For the 48 hour proliferation phase, cells were cultured with ($Ca^{2+}$-independent proliferation) or without ($Ca^{2+}$-dependent proliferation) 10 nM PDB. 1 $\mu$Ci of [$^3$H]-Thymidine (6.7 Ci/mmol; New England Nuclear, Boston, Mass.) was added to each well for the final 16 hours of the assay and at 48 h the cells were harvested and incorporated $^3$H was counted by liquid scintillation counting.

Interleukin-2 Production

Jurkat cells were suspended at a concentration of $2 \times 10^6$ cells/ml in serum-free RPMI-1640 containing 100 U/ml penicillin and 100 $\mu$g/ml streptomycin. Cells were treated for 15 min with the appropriate compound to be tested prior to stimulation with 1 $\mu$g/ml PHA plus 10 nM PDB (calcium-independent) or with PHA alone (calcium dependent). The cells were then incubated for 2 h at 37° C. Following the 2 h stimulation period, the cells were washed twice with RPMI-1640 supplemented with 5% FBS with 5 min incubations between washes and were resuspended at $2 \times 10^6$ cells/ml. The cell suspensions were placed in wells of 24 well plates and were incubated at 37° C. for 24 h. At the end of the incubation, the suspensions were collected, the cells were pelleted and the supernatant was stored at 4° C. for later assay for IL-2 levels.

Interleukin-2 Bioassay

The IL-2 dependent cell line CT-EV was suspended at a concentration of $5 \times 10^4$ cells/ml in modified RPMI-1640 containing 10% FBS, 1 mM L-glutamine, 2-mercaptoethanol, sodium pyruvate and 100 U each of penicillin and streptomycin. 100 $\mu$l of cell suspension were placed in wells of a 96 well plate along with 100 $\mu$l of medium to be tested for IL-2 content. Standard curves were generated by addition of known amounts of recombinant human IL-2 (BioWhittaker) to allow determination of IL-2 content in each sample. Plates were then incubated at 37° C. for 48 h. To determine proliferation of CTEV cells, 1 $\mu$Ci of [$^3$H]-Thymidine (6.7 Ci/mmol; New England Nuclear) was added to each well for the final 16 hours of the assay and at 48 h the cells were harvested and incorporated $^3$H was counted by liquid scintillation counting.

Results

The $Ca^{2+}$ entry pathway in lymphocytes is permeable to $Mn^{2+}$ and is not blocked by amiloride. In several types of electrically non-excitable cells, it has been demonstrated that the $Ca^{2+}$ entry pathway is permeable to $Mn^{2+}$ (Crofts et al, Biochem. J. (1990) 269:579; Fasolato et al, Proc. Natl. Acad. Sci. USA (1993) 90:3068; Hallam et al, Biochem. J. (1988) 255:179; Haverstick et al, Mol. Biol. Cell (1993) 4:173; Kass et al, J. Biol. Chem. (1990) 265:17486; Merritt et al, J. Biol. Chem. (1988) 263:6161; Merritt et al, J. Biol. Chem. (1989) 264:1522). Because $Mn^{2+}$ quenches the fluorescence of common $Ca^{2+}$-sensitive dyes including fura-2 and indo-1, entry of $Mn^{2+}$ into cells containing the dyes is readily monitored. To measure quench of indo-1 by $Mn^{2+}$, fluorescence emission can be monitored at 441 nm, a wavelength that is insensitive to changes in $[Ca^{2+}]_i$ but is sensitive to quenching by $Mn^{2+}$ (Haverstick et al, Mol. Biol. Cell (1993) 4:173). This technique is similar to that used for the related $Ca^{2+}$-sensitive dye fura-2. In contrast to fluorescence emission at 441 nm, emission at 398 nm is related to $[Ca^{2+}]_i$ and fluorescence intensity at this wavelength increases in response to entry of extracellular $Ca^{2+}$ but decreases in response to entry of extracellular $Mn^{2+}$.

Figure 1A:
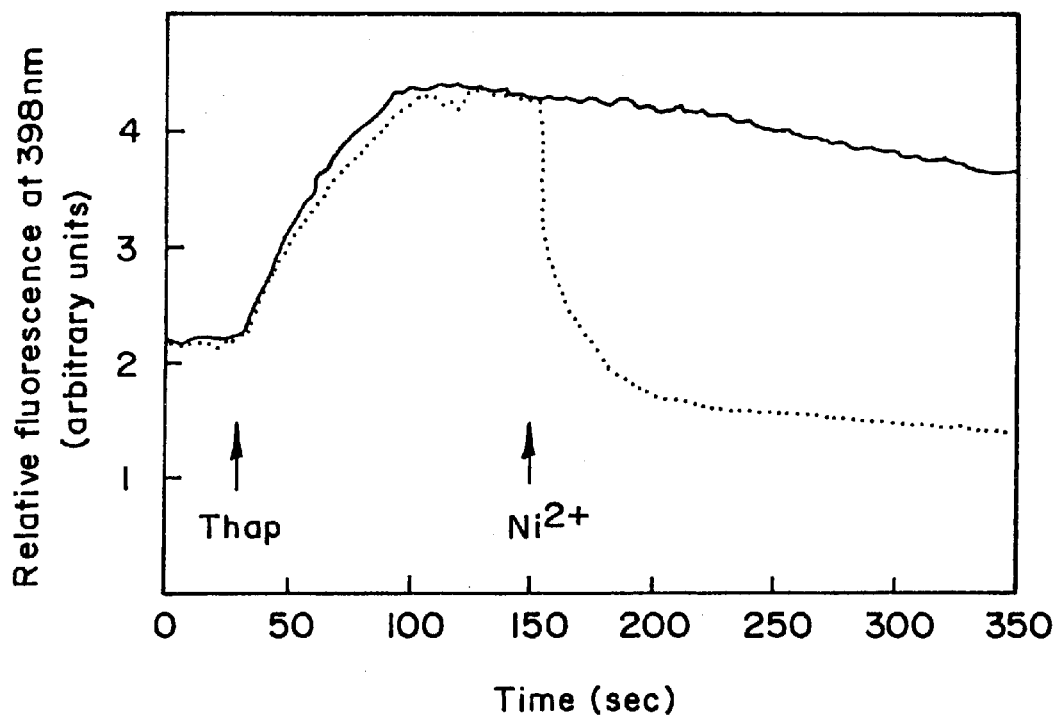
FIGS. 1A–B are graphs depicting how $Mn^{2+}$ permeates the $Ca^{2+}$ pathway in lymphocytes. (A) shows changes in $[Ca^{2+}]_i$ in Jurkat cells stimulated with 300 nM thapsigargin (Thap) as monitored by the fluorescence intensity of indo-1 at 398 nM with no addition (solid line) or with the addition of 5 mM $NiCl_2$ ($Ni^{2+}$) at 150 s to block $Ca^{2+}$ influx (dashed line). (B) shows the quench of indo-1 fluorescence following stimulation of Jurkat cells with 300 nM thapsigargin as measured by monitoring fluorescence at 441 nm. At 250 s, 300 μM $MnCl_2$ ($Mn^{2+}$) was added either in the presence or absence of previously added 5 mM $NiCl_2$ to block the $Ca^{2+}$ entry pathway. Traces are representative of 4 similar experiments.
Figure 1B:
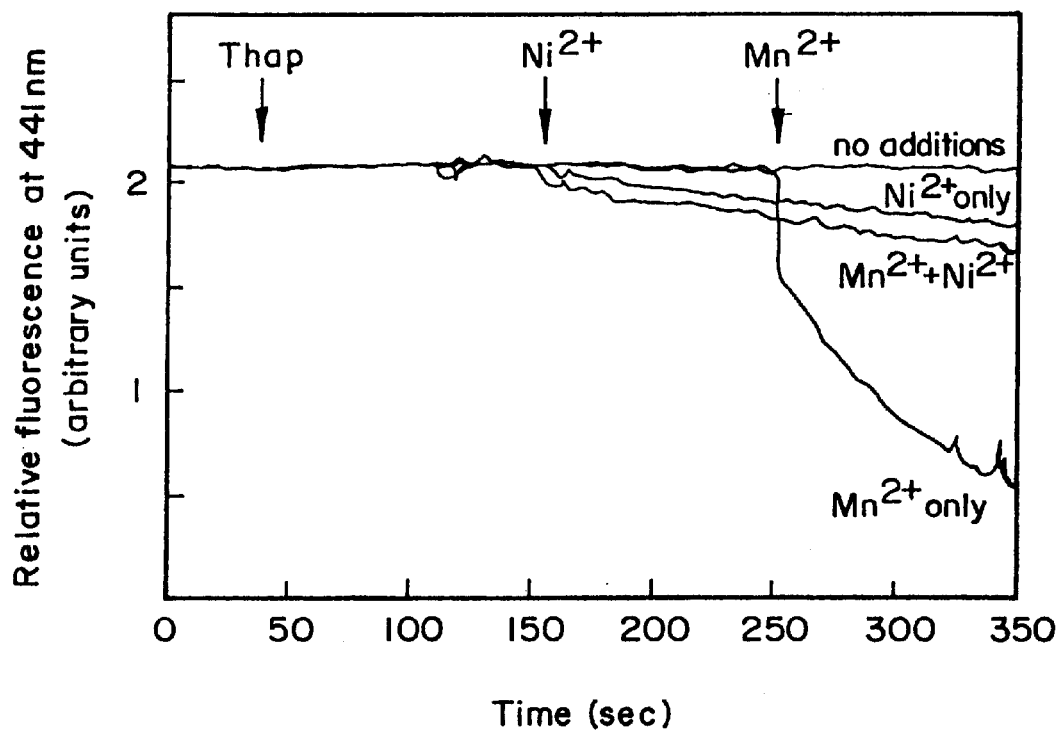

Thapsigargin treatment of lymphocytes results in the initiation of $Ca^{2+}$ entry by a pathway that also allows $Mn^{2+}$ entry. In the presence of extracellular $Ca^{2+}$ but the absence of $Mn^{2+}$, thapsigargin treatment of lymphocytes caused an increase in fluorescence emission at 398 nm as would be expected from an increase in $[Ca^{2+}]_i$ (FIG. 1A). There was, however, no change in fluorescence emission at 441 nm (FIG. 1B) confirming that fluorescence emission at this wavelength does not depend upon $[Ca^{2+}]_i$. However, on addition of 300 $\mu$M $MnCl_2$ to the extracellular medium there was a decrease in fluorescence emission at both 398 nm and 441 nm (FIG. 1B) indicating that extracellular $Mn^{2+}$ had entered the cell interior and quenched the fluorescence emission of indo-1. To further define the route of $Mn^{2+}$ entry, $Ni^{2+}$ was used to block the $Ca^{2+}$ entry pathway. As shown in FIG. 1A, addition of 1 mM $Ni^{2+}$ blocked $Ca^{2+}$ entry and caused $[Ca^{2+}]_i$ to rapidly return to baseline. Because the $Ca^{2+}$ entry pathway is blocked by $Ni^{2+}$, $Mn^{2+}$ quench of the fluorescence emission from indo-1 should be inhibited if extracellular $Mn^{2+}$ enters the cell via this same entry pathway. As shown in FIG. 1B, addition of 1 mM $Ni^{2+}$ to the extracellular medium prevented quench of fluorescence emission from indo-1 by a subsequent addition of $Mn^{2+}$. These data indicate that $Mn^{2+}$ was only able to enter the cell when the $Ca^{2+}$ entry pathway was open. These findings are consistent with observations in a variety of cell types following activation of the $Ca^{2+}$ entry pathway by different agonists and indicate that $Mn^{2+}$ enters through the agonist-linked $Ca^{2+}$ entry pathway.

Figure 2:
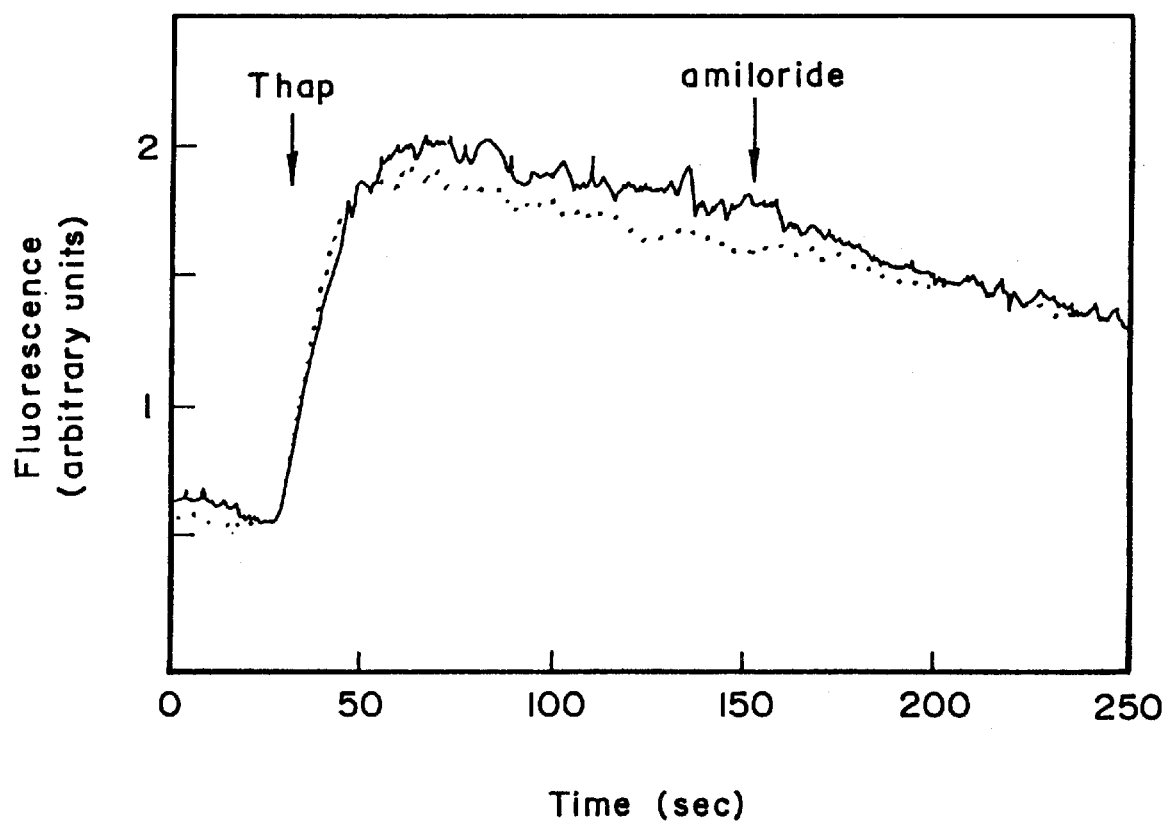
FIG. 2 is a graph depicting how amiloride does not block $Ca^{2+}$ influx stimulated by thapsigargin. Changes in $[Ca^{2+}]_i$ in Jurkat cells were monitored by the fluorescence of fluo-3. At 30 s, 300 nM thapsigargin was added to increase $[Ca^{2+}]_i$ followed by the addition of 100 μM amiloride at 150 s (solid line) or no addition at 150 s (dotted line). Traces are representative of 3 similar experiments.

Extracellular amiloride has been shown to block $Ca^{2+}$ permeation through a $Ca^{2+}$ channel in mouse neuroblastoma and chick dorsal root ganglion cells (Tang et al, Science (1988) 240:213). Because no specific blocker of the $Ca^{2+}$ entry pathway in non-excitable cells has been described, it was of interest to determine the sensitivity of this pathway in lymphocytes to treatment with amiloride. As shown in FIG. 2, addition of 100 $\mu$M amiloride to Jurkat cells at the plateau phase of thapsigargin-stimulated $Ca^{2+}$ entry had no effect on $Ca^{2+}$ influx. Thus, the channel responsible for $Ca^{2+}$ entry in Jurkat cells is relatively insensitive to inhibition by amiloride.

Thapsigargin augments the voltage gated $Ca^{2+}$ current and induces the non-voltage gated current in lymphocytes. We have demonstrated previously that the VG $Ca^{2+}$ current is present in three different human T cell lines as determined by the whole cell variation of the patch clamp technique and that this current is augmented by treatment with a monoclonal antibody to the T cell antigen receptor complex (Densmore et al, FEBS Lett. (1992) 312:161). Because thapsigargin causes an increase in $[Ca^{2+}]_i$ that is similar to that produced by stimulating antibody, it was of interest to examine the VG $Ca^{2+}$ current in Jurkat cells following thapsigargin treatment using the less disruptive perforated patch variation (Horn and Marty, J. Gen. Physiol. (1988) 92:145) of the patch clamp technique (Hamill et al, Pflugers Arch. (1981) 391:85). FIG. 3A shows the current-voltage relation of the VG $Ca^{2+}$ current and demonstrates that the current is indeed voltage gated. The current shown in FIG. 3A is identical to that previously demonstrated to be a $Ca^{2+}$ current in T cells (3), as it is blocked by $Ni^{2+}$, is insensitive to $Na^+$ replacement with $TEA^+$ and shows rapid activation and inactivation. As also shown in FIG. 3A, the magnitude of the whole cell $Ca^{2+}$ current was augmented by the addition of 300 nM thapsigargin. The mean maximum current in unstimulated Jurkat cells was 18.7 pA and increased to 30.6 pA following addition of thapsigargin (n=10, p=0.0019 by the paired Student's t test). Thus, thapsigargin treatment of Jurkat cells augments the VG $Ca^{2+}$ current in a manner similar to stimulation of the T cell receptor.

Figure 3C:
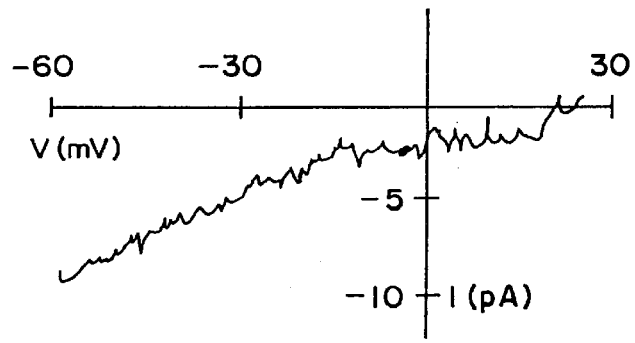

A second inward current observed in T cells is shown in FIG. 3B. This current was induced by thapsigargin treatment of Jurkat cells with the membrane potential held constant at −60 mV in the perforated patch configuration. The current appeared after a short delay and was blocked by addition of extracellular $Ni^{2+}$ (FIG. 3B). The mean maximum magnitude of this current at an imposed membrane potential of −60 mV was 3.6 pA±0.31 (n=38). The current-voltage relation is shown in FIG. 3C and demonstrates that the current was not voltage gated but was inwardly rectifying with no clearly defined reversal potential. These attributes are identical to previous descriptions of this non-voltage gated (NVG) current.

$Mn^{2+}$ has different effects on the VG and NVG currents. Because the $Ca^{2+}$ entry pathway is permeable to $Mn^{2+}$ as demonstrated by $Ca^{2+}$-sensitive dyes, we next examined the capacity of the VG and NVG currents to allow permeation of this ion. As shown in FIG. 4A, the VG $Ca^{2+}$ current was not blocked by the addition of 300 $\mu$M $MnCl_2$ to the extracellular medium. Instead, the VG $Ca^{2+}$ current was increased by about 10% following addition of $Mn^{2+}$ which would be expected from addition of a permeable divalent cation at a concentration of 0.3 mM to medium containing 2 mM $Ca^{2+}$. As also shown (FIG. 4A), addition of $Ni^{2+}$ following $Mn^{2+}$ to medium containing $Ca^{2+}$ eliminated the VG $Ca^{2+}$ current. This inhibition by $Ni^{2+}$ of the VG current that carries $Ca^{2+}$ and $Mn^{2+}$ is identical to the effect of $NF^{2+}$ shown in FIG. 1, in which the $Ca^{2+}$ entry pathway was examined using $Ca^{2+}$-sensitive dyes.

In contrast, the NVG current was reversibly blocked by addition of 300 $\mu$M $MnCl_2$ to the extracellular medium even in the presence of 2 mM $CaCl_2$ (FIG. 4B). Similarly, when extracellular $Ca^{2+}$ was replaced with 2 mM $MnCl_2$ the NVG current did not develop in response to thapsigargin treatment, although the $Ca^{2+}$ entry pathway is open under these conditions. Comparable blockade by $Mn^{2+}$ of an NVG current in mast cells has been reported previously (Hoth and Penner, Nature (1992) 355:353). The experiments shown in FIG. 1 demonstrate that the $Ca^{2+}$ entry pathway as examined by $Ca^{2+}$-sensitive dyes allows passage of $Mn^{2+}$. Similarly, $Mn^{2+}$ does not block and may be carried by the VG $Ca^{2+}$ current while, conversely, the NVG current is essentially eliminated by $Mn^{2+}$ even in the presence of excess $Ca^{2+}$ (FIG. 4).

Amiloride has no effect upon the VG current but blocks the NVG current. As shown in FIG. 2 above, the thapsigargin-initiated $Ca^{2+}$ entry pathway in Jurkat T lymphocytes is not affected by the addition of amiloride to the extracellular medium. Similarly, as shown in FIG. 5A, the VG $Ca^{2+}$ current was not blocked by the addition of an identical concentration of amiloride. In contrast, the NVG current was virtually eliminated by this concentration of amiloride (FIG. 5B). Thus, the $Ca^{2+}$ entry pathway is insensitive to amiloride and the VG $Ca^{2+}$ current is correspondingly unaffected while the NVG current is blocked by this drug.

Augmentation of the VG $Ca^{2+}$ current by thapsigargin is blocked by inhibitors of calmodulin while the NVG current is unaffected. Using $Ca^{2+}$-sensitive dyes, we have previously demonstrated that initiation of $Ca^{2+}$ influx in Jurkat cells is inhibited by agents that interfere with calmodulin (CaM) activation, such as the phenothiazines or the structurally and mechanistically unrelated compound W-7 (Haverstick et al, Mol. Biol. Cell (1993) 4:173). Because inhibitors of CaM prevented initiation of $Ca^{2+}$ entry by thapsigargin as measured by a $Ca^{2+}$-sensitive dye, we examined the effect of these agents on the VG and NVG currents. The unstimulated VG $Ca^{2+}$ current was not affected by treatment with W-7 alone. However, as shown in FIG. 6A, prior addition of W-7 blocked the augmentation of the current that is normally induced by thapsigargin (FIG. 3A). The phenothiazine trifluoperazine, which also blocks initiation of the $Ca^{2+}$ entry pathway, also prevented the increase in the VG current following thapsigargin addition. Both trifluoperazine and W-7 blocked the thapsigargin-mediated augmentation of the VG $Ca^{2+}$ current at concentrations previously shown to inhibit initiation of $Ca^{2+}$ influx.

In contrast to the augmentation of the VG $Ca^{2+}$ current, the appearance of the NVG current in response to thapsigargin treatment was not affected by prior addition of W-7 (FIG. 6B). As determined by $Ca^{2+}$-sensitive dyes, the addition of W-7 or any one of three phenothiazines eliminates $Ca^{2+}$ influx induced by thapsigargin. Because the NVG current was induced by thapsigargin under conditions which eliminate $Ca^{2+}$ entry, these observations further suggest that the NVG current does not account for $Ca^{2+}$ entry via the pathway defined by $Ca^{2+}$-sensitive dyes.

Nordihydroguaiaretic acid blocks the $Ca^{2+}$ entry pathway and the VG $Ca^{2+}$ current but does not affect the NVG current. Sensory neurons (Fox et al, J. Physiol. (Lond.) (1987) 394:149; Fox et al, J. Physiol. (Lond.) (1987) 394:173), pituitary gland cells (Korn et al, Mol. Pharmacol. (1990) 38:524) and fibroblasts (Estacion and Morgan, Cell Calcium (1993) 14:161; Wang et al, Am. J. Physiol. (1993) 265:C1239) have a T type voltage gated $Ca^{2+}$ current with properties similar to that of the VG $Ca^{2+}$ current in lymphocytes. In pituitary gland cells and fibroblasts, nordihydroguaiaretic acid (NDGA) inhibits $Ca^{2+}$ entry via this T type $Ca^{2+}$ current. Although NDGA suppresses arachidonic acid metabolism in several systems, its blockage of T type voltage gated $Ca^{2+}$ channels was shown to be independent of effects on the arachidonic acid pathway. Because the VG $Ca^{2+}$ current has characteristics similar to T type $Ca^{2+}$ currents in other systems, it was of interest to examine the effects of NDGA on $Ca^{2+}$ entry in lymphocytes. As shown in FIG. 7A, addition of NDGA to Jurkat cells inhibited $Ca^{2+}$ entry stimulated by thapsigargin as determined by indo-1. This was not due to an effect on dye fluorescence because NDGA did not alter indo-1 fluorescence as determined by the fluorescence spectrum of the free acid form of the dye. The $IC_{50}$ for NDGA blockade of thapsigargin-stimulated $Ca^{2+}$ entry was 5 $\mu$M (n=10, $r^2$=0.995), a value similar to that reported for inhibition of $Ca^{2+}$ entry via a T type voltage gated $Ca^{2+}$ current in fibroblasts (49). Similarly, treatment of Jurkat cells with NDGA inhibited the VG $Ca^{2+}$ current by about 70% (FIG. 7B). The magnitude of inhibition of the VG $Ca^{2+}$ current is virtually identical to that shown for inhibition of a T type $Ca^{2+}$ channel in pituitary gland cells and fibroblasts. However unlike inhibition of $Ca^{2+}$ entry monitored by $Ca^{2+}$-sensitive dyes (FIG. 7A) and suppression of the VG $Ca^{2+}$ current (FIG. 7B) by NDGA, addition of this reagent had no effect upon the thapsigargin-induced NVG current (FIG. 7C). Thus, NDGA inhibited thapsigargin-induced $Ca^{2+}$ entry as determined by $Ca^{2+}$-sensitive dyes, suppressed the thapsigargin-augmented VG $Ca^{2+}$ current but had no effect on the thapsigargin-initiated NVG current.

NDGA blocks $Ca^{2+}$ dependent, but not $Ca^{2+}$ independent, proliferation and lymphokine production. T cells can be stimulated to proliferate in a $Ca^{2+}$-dependent or a $Ca^{2+}$-independent manner using appropriate combinations of a mitogen and protein kinase C activator (Dupuis et al, J. Physiol. (Lond.) (1989) 412:135; Kumagai et al, J. Cell. Physiol. (1988) 137:329). Stimulation of proliferation of peripheral blood mononuclear cells (PBMC) by the T cell mitogen PHA in combination with phorbol dibutyrate (PDB) for 1 h followed by medium alone for 48 h requires the presence of extracellular $Ca^{2+}$ during the initial treatment with PHA and PDB. However, treatment with PHA and PDB followed by PDB for 48 h stimulates proliferation even in the absence of extracellular $Ca^{2+}$ during the initial 1 h treatment (FIG. 8). As shown in FIG. 8 (closed bars), addition of NDGA during treatment of PBMC using the $Ca^{2+}$-dependent protocol inhibited proliferation while there was no effect of NDGA treatment on $Ca^{2+}$-independent proliferation (FIG. 8, open bars). The $IC_{50}$ for inhibition of proliferation by NDGA was approximately 3 $\mu$M (n=6), similar to the value obtained for blockade of $Ca^{2+}$ entry as well as for inhibition of the VG $Ca^{2+}$ current (FIG. 7). Inhibitors of lipoxygenase and cyclooxygenase did not mimic this effect of NDGA (FIG. 8) indicating that the effect of NDGA on proliferation was not due to inhibition of arachidonic acid metabolism. The effect of NDGA on proliferation was similar to that seen with the $Ca^{2+}$ chelator, EGTA or CsA (FIG. 8). Because none of these treatments had an effect on $Ca^{2+}$-independent proliferation, the data confirm the idea that NDGA blocks $Ca^{2+}$-dependent signalling initiated by an activating stimulus.

Jurkat cells secrete IL-2 in either a $Ca^{2+}$-dependent or -independent fashion in response to treatment with PHA and PDB as just described. As shown in FIG. 9, NDGA suppressed IL-2 secretion when the cells were stimulated in a $Ca^{2+}$-dependent fashion and had little effect on the stimulus that did not initially require extracellular $Ca^{2+}$. Similar to proliferation, inhibition of IL-2 secretion by NDGA paralleled that caused by either CsA or extracellular EGTA (FIG. 9). As with proliferation, inhibition of arachidonic acid metabolism by a combination of ASA and phenidone (FIG. 9) or indomethacin and phenidone had no effect on IL-2 secretion. Thus, $Ca^{2+}$-dependent proliferation of PBMC as well as $Ca^{2+}$-dependent secretion of IL-2 by Jurkat T cells can be blocked by an inhibitor of the VG $Ca^{2+}$ current, NDGA. These observations indicate that NDGA, most likely via inhibition of $Ca^{2+}$ influx through the VG $Ca^{2+}$ current, can suppress $Ca^{2+}$-dependent T cell activation.

Example 2

The Effect of Inhibition of Calmodulin Function on Increased Intracellular Calcium and Cellular Proliferation

TABLE $IC_{50}$ values for phenothiazine effects

| | JURKAT | | MDA-468 | |
|---|---|---|---|---|
| DRUG | $[Ca^{2+}]_i^a$ | prolif[b] | $[Ca^{2+}]_i^c$ | prolif[d] |
| trifluoroperazine | 3.3 $\mu$M | 5.4 $\mu$M | 1 $\mu$M | 20 $\mu$M |
| chloropromazine | 25 $\mu$M | 90 $\mu$M | 5 $\mu$M | 20 $\mu$M |
| promethazine | 65 $\mu$M | 3.5 $\mu$M | 105 $\mu$M | 30 $\mu$M |

[a]The effect of phenothiazine treatment on the maximal $[Ca^{2+}]_i$ reached following antigen receptor engagement was determined by treating Jurkat cells for 1 min with the indicated phenothiazine prior to treatment with the anti-CD3 mAb OKT3. Percent inhibition was calculated compared with increase in $[Ca^{2+}]_i$ seen in the absence of phenothiazine treatment. Half-maximal inhibitory concentrations were determined using GraphPad software (San Diego, CA).
[b]The effect of phenothiazine treatment on the proliferation of Jurkat cells was determined by incubation of Jurkat cells with various concentrations of the indicated phenothiazine for 44 to 48 h. Cell number was determined using the protocol outlined in Example 4 and compared to cells grown in the absence of phenothiazines. Half-maximal inhibitory concentrations were determined using GraphPad software (San Diego, CA).
[c]The effects of phenothiazine treatment on the maximal $[Ca^{2+}]_i$ reached was determined as for Jurkat cells above, except that the $Ca^{2+}$ entry pathway was triggered by 50 ng/ml EGF.
[d]The effects of phenothiazine treatment on the proliferation of MDA-468 human breast cancer cells was determined by incubation of the cells with various concentrations of the indicated phenothiazine for 44 to 48 h. Inhibition was determined as for Jurkat cells above.

The effect of the phenothiazine promethazine on the proliferation of the human prostate cancer cell line PC3 was determined by incubating $5\times10^4$ PC3 cells with the indicated concentrations of promethazine for 48 hours. The number of viable cells remaining at the end of the incubation period was evaluated using the protocol outlined in Example 4. EGTA (2 mM) was included as a positive control. Based on this experiment, the $IC_{50}$ of promethazine is roughly 40 $\mu$M.

Example 3

Effect of Blockage of the Voltage Gate Calcium Channel on Cellular Proliferation The effect of various drugs on the proliferation of Jurkat T cells, MDA-468 human breast cancer cells and PC3 human prostate cancer cells was determined by incubating the cells with the indicated concentrations of drug for 48 hours. The number of viable cells remaining at the end of the incubation period was evaluated using the procedure outlined in Example 4.

TABLE

Drugs examined for effects on calcium influx and cellular proliferation

| DRUG | T cell $[Ca^{2+}]_i$ [a] | T cell PROLIF [b] | MDA $[CA^{2+}]_i$ [c] | MDA PROLIF [d] |
|---|---|---|---|---|
| 3-methoxy, 4-hydroxyphenylethanol | NE | ND | ND | NE |
| 3-methoxy, 4-hydroxyphenylglycerol | NE | ND | ND | NE |
| amrinone | NE | ND | ND | NE |
| bepridil | ↓ (post) | ↓ | ↑ | ↓ |
| no INDO effects | NE (pre) | | | |
| bupropion | NE | NE | ND | NE |
| chlorcyclizine | NE | ND | ↑ | ↓ |
| cinnarizine | ↓ | ↓ | NE | NE |
| no INDO effects | | | | |
| curcumin | XX | ↓ | XX | NE |
| affects INDO-use FUFL | | | | |
| cyclizine | NE | ND | ND | NE |
| datrolene | NE | ND | NE | NE |
| diethylcarbamazine | NE | NE | NE | NE |
| fendiline | ↓ | ↓ | ↑ | ↓ |
| no INDO effects | | | | |
| flunarizine | ↓ | ↓ | NE | NE |
| no INDO effects | | | | |
| fluphenazine | ↓ | ↓ | ↓ | ↓ |
| no INDO effects | | | | |
| hydroxyzine | NE | NE | ND | NE |
| no INDO effects | | | | |
| isradipine | ↓ | NE | ND | NE |
| no INDO effects | | | | |
| lidoflazine | ↓ | ↓ | ND | (↓) |
| affects INDO-use FUFL | | | | |
| meclizine | ↓ (post) | (↓) | ND | NE |
| no INDO effects | NE (pre) | | | |
| mianserin | NE | NE | ND | NE |
| NDGA | ↓ | ↓ | ↓ | ↓ |
| no INDO effects | | | | |
| nicardipine | ↓ | ↓ | NE | (↓) |
| no INDO effects | | | | |
| niflumic acid | ↓ (post) | (↓) | ND | NE |
| no INDO effects | NE (pre) | | | |
| perhexiline | ↑ (post) | ↓ | ↑ | ↓ |
| no INDO effects | ↓(pre) | | | |
| pipenidic acid | NE | NE | ND | NE |
| affects INCO-use FUFL | | | | |
| prenylamine lactate | ↓ (post) | ↓ | ↑ | ↓ |
| no INDO effects | ↓(pre) | | | |
| quipazine | NE | ND | ND | NE |
| affects INDO-use FUFL | | | | |
| silymarin group | NE | NE | ND | NE |
| tetranethylpyrazine | NE | ND | ND | NE |
| tetrandrine | ↓ (post) | ↓ | ↓ (post) | ↓ |
| no INDO effects | NE (pre) | | NE (pre) | |
| trazodone | NE | NE | ND | NE |
| affects INDO-use FUFL | | | | |

[a] The effect of the drug added post- or pre- T cell receptor stimulation on the normally occurring changes in $[Ca^{2+}]_i$. Unless otherwise indicated, the effect was the same post- and pre- receptor stimulation.
[b] The effect of the drug on T cell proliferation.
[c] The effect of the drug added post- or pre- EGF receptor stimulation on the normally occurring changes in $[Ca^{2+}]_i$. Unless otherwise indicated, the effect was the same post- and pre- receptor stimulation.
[d] The effect of the drug on human breast cancer cell proliferation.
NE - no effect
ND - not determined

Example 4
Technical Overview of Drug Screening Protocol

Compounds can be screened for antiproliferative activity by examining changes in intracellular calcium in Jurkat T cells and the effect of these compounds on proliferation of MDA-468 cells, a human breast cancer cell line. Compounds found to have an effect in this initial screen can then be examined for effects on proliferation of Jurkat T cells and epidermal growth factor receptor initiated changes in intracellular calcium in MDA-468 cells.

Effect of Drugs on Receptor-stimulated $Ca^{2+}$ Influx

Initially, all drugs are screened using Jurkat T cells incubated with indo-1/AM as outlined below. In the event that there is an effect of the drug on the maximum $[Ca^{2+}]_i$ reached following treatment of the cells with the anti-CD3 mAb OKM, the drug is evaluated for any effects on the spectral characteristics of indo-1 as outlined in Haverstick and Gray, Mol. Biol. Cell (1993) 4:173. If there is an effect of the drug on the spectral characteristics of indo-1, the drug is further examined for spectral effects on the combination of fura-red and fluo-3. If there is no effect of the drug on the fura-red/fluo-3 combination, the drug is examined for effects on the maximum $[Ca^{2+}]_i$ reached following OKT3 treatment of cells incubated with 5 μM fura-red and 10 μM fluo-3 as outlined below.

Jurkat cells are incubated in RPMI-1640 plus 5% fbs in the presence of the acetoxymethyl ester of either indo-1 (1 μM) or the combination of fura-red (5 μM) with fluo-3 (1 μM) for one hour at 37° C. Cells are washed three times in buffer A [10 μM 4-(2-hydroxyethyl)-1-piperazine ethane-sulfonic acid (HEPES), pH 7.4, 3 MM KCl, 1 mM $MgCl_2$, 1 mM $CaCl_2$, 140 mM NaCl, 0.1% glucose] containing 1% fbs and suspended to a final concentration of $1 \times 10^6$/ml. Cells are then placed in the 37° C. jacketed cell holder of the SLM 8000C. Antigen receptor engagement is mimicked by the addition of the anti-CD3 monoclonal antibody OKT3 (Gray et al, J. Exp. Med. (1988) 167:1963; Gray et al, J. Immunol. 142:1631). The effect of drug added prior to receptor stimulation or at the plateau phase of $Ca^{2+}$ entry is determined as follows:

Control: 6 μl vehicle @ 30 seconds, 1 μg/ml OKT3 at 90 seconds
Prior drug: 10 or 30 μM drug @ 30 seconds, 1 μg/ml OKT3 at 90 seconds
Post drug: 1 μg/ml OKT3 at 30 second, 10 or 30 μM drug @ 120 seconds
Control: 1 μg/ml OKT3 at 30 seconds, 6 μl vehicle @ 120 seconds Excitation and emission wavelengths for the two dye schemes are shown in the following table. The ratiometric measurements are converted to $[Ca^{2+}]_i$ measurements according to the previously published calculations (Engelhard et al, Ann. N.Y. Acad. Sci. 532:303.

| DYE | Excitatian λ | Emission λ (A/B) |
|---|---|---|
| indo-1 | 340 | 398/480 |
| fura-red/fluo-3 | 488 | 525/650 |

MDA468 cells are incubated with either indo-1 or the combination of fura-red/fluo-3 for 1 hour while still adherent in the maintenance flask in DMEM plus 5% fbs and 1 μg/ml insulin. Cells are removed by gentle scraping and washed three times in buffer A containing 1% charcoal stripped fbs (Nelson et al, Br. J. Cancer (1991) 63:933). The cells are then suspended to a final concentration of 1e6/ml and used as above in the SLM. For the human breast cancer cells, $Ca^{2+}$ entry is stimulated by the addition of 25 ng/ml EGF, rather than the antibody used above.

Effect of Drugs on Normal Cellular Proliferation

Cells are plated in triplicate in a 96-well flat-bottomed plate (Jurkat: 5e4 cells/well in RPMI-1640 plus 5% fbs; MDA468: 2.5e4 per well in DMEM plus 5% fbs and 11 μg/ml insulin) in the absence (control) or presence of drug at 3, 10, 30, and 100 μM. An additional control of 100 μM drug in RPMI-1640 plus 5% fbs or DMEM plus 5% fbs and 11 μg/Ml insulin with no cells is included with each run to control for possible drug interactions with the dye. The plate is then placed in a 5% $CO_2$ 37° C. incubator for 44 to 48 hours. 20 μl of dye solution containing a tetrazolium dye (3-(4,5-dimethylthiazol-2-yl)-5-(3-carboxymethoxyphenyl)-2-(4-sulfophenyl)-2H-tetrazolium, Owen's reagent) plus coupling reagent (phenazine methosulfate) is added to each well, the plate is returned to the incubator, and the absorbance at 490 nm is read using an ELISA plate reader 3 to 4 h (Jurkat cells) or 2 to 3 h (MDA-468 cells) later. All data are presented as percent of control (no drug addition). With this protocol, it is possible to determine the effect of 5 drugs at 4 concentrations in a single 96-well plate as outlined below:

|   | 1–3 | 4–6 | 7–9 | 10–12 |
|---|---|---|---|---|
| A | buffer | 10 μM | 100 μM | 3 μM |
| B | control | 3 μM | 30 μM | (buffer + 100 μM) |
| C | control | (buffer + 100 μM) | 10 μM | 100 μM |
| D | 1 mM EGTA | 100 μM | 3 μM | 30 μM |
| E | 2.5 mM EGTA | 30 μM | (buffer + 100 μM) | 10 μM |
| F | (buffer + 100 μm) | 10 μM | 100 μM | 30 μM |
| G | 100 μM | 3 μM | 30 μM | |
| H | 30 μM | (buffer + 100 μM) | 10 μM | |

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A method of inhibiting calcium entry into electrically non-excitable cells selected from the group consisting of lymphocytes, epithelial cells, connective tissue cells, secretory cells, Jurkat T-cells, MDA-468 cells and PC-3 cells comprising administering a voltage gated (VG) selective inhibitor in an amount of about 1 μM to about 100 μM.

2. A method for preventing proliferation of electrically non-excitable cells comprising administering a voltage gated (VG) selective inhibitor wherein said VG-selective is cinnarizine.

3. A method for treating autoimmune diseases comprising administering to a patient in need thereof, a voltage gated (VG) selective inhibitor wherein said VG-selective is cinnarizine and a pharmaceutical carrier, wherein said voltage gated inhibitor is present in an amount effective to prevent the proliferation of electrically non-excitable cells.

4. A method for preventing graft rejection comprising administering to a patient in need thereof, a voltage gated (VG) selective inhibitor wherein said VG-selective inhibitor is cinnarizine and a pharmaceutical carrier, wherein said voltage gated inhibitor is present in an amount effective to prevent the proliferation of electrically non-excitable cells.

5. A method for treating cancer comprising administering to a patient in need thereof, a voltage gated (VG) selective inhibitor wherein said VG-selective inhibitor is cinnarizine and a pharmaceutical carrier, wherein said voltage gated inhibitor is present in an amount effective to prevent the proliferation of electrically non-excitable cells.

6. The method of claim 1, wherein said VG-selective inhibitor is a piperazine.

7. The method of claim 6, wherein said piperazine is cinnarizine.

8. A method of reducing proliferation of electrically non-excitable cells selected from the group consisting of lymphocytes, epithelial cells, connective tissue cells, secretory cells, Jurkat T-cells, MDA-468 cells and PC-3 cells comprising administering a voltage gated (VG) selective inhibitor to electrically non-excitable cells in an amount of about 1 µm to about 100 µm.

* * * * *

UNITED STATES PATENT AND TRADEMARK OFFICE
CERTIFICATE OF CORRECTION

PATENT NO. : 6,413,967 B1
DATED : July 2, 2002
INVENTOR(S) : Lloyd Gray et al.

It is certified that error appears in the above-identified patent and that said Letters Patent is hereby corrected as shown below:

<u>Column 1,</u>
Line 5, insert the following:

-- The research on which the technology described herein is based was supported in-part by the U.S. government funding National Cancer Institute. The government may have certain rights in this application. --

Signed and Sealed this

Eleventh Day of February, 2003

JAMES E. ROGAN
*Director of the United States Patent and Trademark Office*